(12) United States Patent
Tung et al.

(10) Patent No.: US 10,183,097 B2
(45) Date of Patent: Jan. 22, 2019

(54) ENGINEERED CARDIAC DERIVED COMPOSITIONS AND METHODS OF USE

(71) Applicant: THE JOHNS HOPKINS UNIVERSITY, Baltimore, MD (US)

(72) Inventors: Leslie Tung, Columbia, MD (US); Adriana Blazaski, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 30 days.

(21) Appl. No.: 15/039,577

(22) PCT Filed: Nov. 26, 2014

(86) PCT No.: PCT/US2014/067657
§ 371 (c)(1),
(2) Date: May 26, 2016

(87) PCT Pub. No.: WO2015/081226
PCT Pub. Date: Jun. 4, 2015

(65) Prior Publication Data
US 2017/0173215 A1    Jun. 22, 2017

Related U.S. Application Data

(60) Provisional application No. 61/909,715, filed on Nov. 27, 2013.

(51) Int. Cl.
*A61L 27/36* (2006.01)
*A61L 27/38* (2006.01)
(Continued)

(52) U.S. Cl.
CPC ....... *A61L 27/3826* (2013.01); *A61L 27/3683* (2013.01); *A61L 27/3804* (2013.01);
(Continued)

(58) Field of Classification Search
CPC .................... A61L 27/3633; A61L 27/3625
See application file for complete search history.

(56) References Cited

U.S. PATENT DOCUMENTS

| | | |
|---|---|---|
| 8,470,520 B2 | 6/2013 | Ott et al. |
| 2002/0022878 A1 | 2/2002 | Orton |

(Continued)

FOREIGN PATENT DOCUMENTS

| | | |
|---|---|---|
| WO | 2006095342 A2 | 9/2006 |
| WO | 2012170490 A2 | 12/2012 |

(Continued)

OTHER PUBLICATIONS

University of Florida, untitled reference, ref. No. 11 from the Wikipedia entry for Flash Freezing, https://web.archive.org/web/20120111233417/http://www.biotech.ufl.edu/EM/data/freeze.html Jan. 11, 2012.*

(Continued)

*Primary Examiner* — Rosanne Kosson
(74) *Attorney, Agent, or Firm* — John Hopkins Technology Ventures

(57) ABSTRACT

The present invention establishes a new standard for investigative studies of patient-specific, genetic cardiac diseases at a functional, tissue level by creating a novel platform for the study of cardiac related diseases, including cardiac conduction dysfunction, arrhythmias and depressed contractility for example. Provided herein are novel compositions of human engineered heart slices (EHS) formed from thin slices of decellularized cardiac tissue. Also included are compositions comprising a hybrid of decellularized tissue and organotypic organ slice technology. Intact mammalian hearts are precision cut to obtain thin slices in a range of thicknesses, decellularized, and seeded with various mammalian cells which can be from a variety of sources. Methods of investigation of many diseases and methods of use of (Continued)

these compositions for screening compounds for therapeutic purposes are also provided.

39 Claims, 19 Drawing Sheets

(51) Int. Cl.
*A61L 27/54* (2006.01)
*C12Q 1/37* (2006.01)
*G01N 33/50* (2006.01)

(52) U.S. Cl.
CPC ....... *A61L 27/3808* (2013.01); *A61L 27/3834* (2013.01); *A61L 27/3886* (2013.01); *A61L 27/54* (2013.01); *C12Q 1/37* (2013.01); *G01N 33/5061* (2013.01); *A61L 2300/414* (2013.01); *A61L 2430/20* (2013.01)

(56) References Cited

U.S. PATENT DOCUMENTS

| | | |
|---|---|---|
| 2006/0104958 A1 | 5/2006 | Akins |
| 2009/0202977 A1* | 8/2009 | Ott ................. C12N 5/0657 435/1.2 |
| 2011/0189140 A1 | 8/2011 | Christman et al. |
| 2012/0115226 A1 | 5/2012 | Stachelsheid et al. |
| 2013/0164266 A1 | 6/2013 | Jensen |
| 2015/0037434 A1 | 2/2015 | Freytes et al. |

FOREIGN PATENT DOCUMENTS

| | | |
|---|---|---|
| WO | 2013-028968 A1 | 2/2013 |
| WO | 2013018021 A1 | 2/2013 |
| WO | 2013151755 A1 | 10/2013 |

OTHER PUBLICATIONS

Blazaski, A., et al. (2012) "Cardiomyocytes derived from human induced pluripotent stem cells as models for normal and diseased cardiac electrophysiology and contractility" Progress in Biophysics and Molecular Biology, vol. 110, No. 2, pp. 166-177.
Carvalho, J., et al. (2012) "Characterization of decellularized heart matrices as biomaterials for regular and whole organ tissue engineering and initial in-vitro recellularization with Ips cells" Tissue Science & Engineering, vol. 11, pp. 1-5.
Zimmerman, W, et al., Three-Dimensional Engineered Heart Tissue from Neonatal Rat Cardiac Myocytes. Biotechnology and Bioengineering. (2000) vol. 68, Iss. 1: 106-114.
Ott, H., et al., Perfusion-decellularized matrix: using nature's platform to engineer a bioartificial heart. Nature Medicine. (2008) vol. 14: 213-221.
Rieder, E., et al., Decellularized Porcine and Human Valve Scaffolds Differ Importantly in Residual Potential to Attract Monocytic Cells, Circulation (2005) vol. 111: 2792-2797.
Schenke-Laylands, et al., (2003) Impact of decellularization of xenogeneic tissue on extracellular matrix integrity or tissue engineering of heart valves. Journal of Structural Biology. vol. 143, Iss. 3: 201-208.
Vukadinovic-Nikolic, Z., et al., (2013) Generation of Bioartificial Heart Tissue by Combining a Three-Dimensional Gel-Based Cardiac Construct with Decellularized Small Intestinal Submucosa. Tissue Engineering Part A. E-publication.
Lu, T., et al., (2013) Repopulation of decellularized mouse heart with human induced pluripotent stem cell-derived ;cardiovascular progenitor cells. Nature Comunications. vol. 4: 2307.
Eschenhagen, T., et al., (2002) 3D engineered heart tissue for replacement therapy. Basic Research in Cardiology. vol. 97, Iss. 1: 146-153.
Singelyn, J., et al., (2009). Naturally derived myocardial matrix as an injectable scaffold for cardiac tissue engineering. Biomaterials. vol. 30, Iss. 29: 5409-5416.
Rajabi-Zeleti, S., et al., (2014). The behavior of cardiac progenitor cells on macroporous pericardium-derived scaffolds. Biomaterials. vol. 35, Iss 4: 970-982.
Zhou J. et al (2013). Tissue engineering of heart valves: PEGylation of decellularized porcine aortic valve as a scaffold for in vitro recellularization. Biomedical Engineering Online. vol. 12, Iss. 1: 87.
Schaaf, S., et al., Human engineered heart tissue as a versatile tool in basic research and preclinical toxicology. PLoS One. 2011;6:e26397.
Deboer, T., et al., Myocardial tissue slices: organotypic pseudo-2D models for cardiac research & development. Future Cardiol. 2009;5:425-30.
Gilbert, T., et al., Decellularization of tissues and organs. Biomaterials. 2006;27:3675-83.
Crapo, P., et al., An overview of tissue and whole organ decellularization processes. Biomaterials. 2011;32:3233-43.
Akhyari, P., et al., The quest for an optimized protocol for whole-heart decellularization: a comparison of three popular and a novel decellularization technique and their diverse effects on crucial extracellular matrix qualities. Tissue Eng Part C Methods. 2011;17:915-26.
Stevens, K., et al., Physiological function and transplantation of scaffold-free and vascularized human cardiac muscle tissue. Proc Natl Acad Sci U S A. 2009;106:16568-73.
Wainwright, J., et al., Preparation of cardiac extracellular matrix from an intact porcine heart. Tissue Eng Part C Methods. 2010;16:525-32.
Eitan, Y., et al., Acellular cardiac extracellular matrix as a scaffold for tissue engineering: In-vitro cell support, remodeling and biocompatibility. Tissue Eng Part C Methods. 2010;16:671-83.
Zhang, D. et al., Tissue-engineered cardiac patch for advanced functional maturation of human ESC-derived cardiomyocytes. Biomaterials. 2013;34:5813-20.
Zimmermann, W., et al., Engineered heart tissue grafts improve systolic and diastolic function in infarcted rat hearts. Nat Med. 2006;12:452-8.
Kawamura, M., et al., Feasibility, safety, and therapeutic efficacy of human induced pluripotent stem cell-derived cardiomyocyte sheets in a porcine ischemic cardiomyopathy model. Circulation. 2012;126:S29-37.

* cited by examiner

ENGINEERED CARDIAC DERIVED COMPOSITIONS AND METHODS OF USE

CROSS-REFERENCE TO RELATED APPLICATIONS

This application is a 35 U.S.C. § 371 U.S. national entry of International Application PCT/US2014/067657, having an international filing date of Nov. 26, 2014, which claims the benefit of U.S. Provisional Application No. 61/909,715, filed Nov. 27, 2013, the content of each of the aforementioned applications is herein incorporated by reference in their entirety.

BACKGROUND OF THE INVENTION

For over a decade, the engineering of human muscle and cardiac tissue constructs has been an active area of innovation and development because of their enormous promise in the fields of regenerative medicine, drug development and basic research. A straightforward and direct approach to create tissue constructs would be to cut and maintain live tissue slices from explanted human hearts or tissue biopsies. This has been shown to be feasible in recent years from animal hearts, but for human tissue this approach faces enormous hurdles in terms of cellular damage created by cutting, short shelf life of cut tissues, limited availability and quantities of source material, and immunogenic responses.

The next best strategy is to create scaffolds onto which cells such as cardiac cells, for example, can be engrafted at the time of need. These scaffolds can be synthetic (derived from artificial materials such as polymers), or natural (derived from decellularized intact tissue). The latter are advantageous because they are biocompatible and possess mechanical and biochemical properties that are physiological, all of which have been difficult to reproduce so far in synthetic scaffolds Immunogenic responses are greatly muted, if not eliminated, with removal of the cellular component. Many methods have been developed to decellularize tissues from various organs, including the use of physical methods (e.g., freezing, pressure, tonicity), or chemical methods (acids, detergents, enzymes, chelators). In heart, decellularization has generally been applied to the whole organ to take advantage of the coronary vasculature as a means to effectively perfuse the tissue, beginning with a seminal study by Ott and colleagues (Ott, H. C. et al, *Nature Medicine* 14:213-21, 2008) that used SDS detergent, with alternative procedures by Wainwright and colleagues (Wainwright, J. M. et al, *Tissue Engineering. Part C, Methods* 16:525-532, 2010) using a complex hypotonic, hypertonic, enzyme, acid and detergent treatment. One study precut pig hearts into 3 mm thick slices prior to decellularization (Eitan, Y. et al., *Tissue Engineering. Part C, Methods*, 16(4), 671-83). In general, decellularization procedures leave behind an extracellular matrix scaffold that is biocompatible with low cell toxicity, and an ongoing challenge is to remove the residual cells without adversely affecting the matrix. The decellularized tissue can be dried and formed into an extracellular matrix powder, which can then be reconstituted as a gel in which cardiac cells can be suspended, grown and injected into the heart. Several companies have developed decellularized tissue products for clinical use, including: ACell (Columbia, Md.), marketing decellularized tissue matrix derived from urinary bladder of pigs, Ventrix (San Diego, Calif.), marketing an injectable gel created from extracellular matrix powder derived from pig hearts, Wright Medical Technology Inc. (Arlington, Tenn.), marketing acellular grafts from donated human skin for soft tissue replacement, Stryker (Kalamazoo, Mich.) marketing an acellular collagen membrane from human dermis for soft tissue repair, and Braun Melsungen AG (Melsungen, Germany), marketing a collagen implant from bovine pericardium for connective tissue substitution.

Cells grown in a 3D environment are widely acknowledged to experience important signaling cues that are lacking in conventional flat, 2D cultures. Four methods have already emerged to create relatively functional 3D cardiac tissue constructs: gels seeded with cardiac cells to create strands or rings of tissue, cardiac tissue patches created from stacks of cell sheets, scaffold-free clusters or patches created by aggregates of large numbers of cardiomyocytes, and compaction of cells into a mesh-like network. In general, only narrow strands or rings of gels seeded with cardiac cells have succeeded so far in producing an alignment of cells along a common axis, which is very important for efficient muscle function.

Therefore, there still exists an unmet need for 3D culture platforms and methods which even more closely recapitulate the in vivo microenvironment.

SUMMARY OF THE INVENTION

The present invention provides novel compositions which are termed "engineered heart slices" (EHS). In accordance with some embodiments, the present invention provides novel compositions which comprise decellularized cardiac tissue matrix derived from mammalian heart slices. The tissue matrix can be prepared from live or cadaver heart tissue and prepared as slices of varying thickness. In some embodiments, the slices can then be dried, frozen, and stored for subsequent use with appropriate reconstitution.

In accordance with other embodiments, the present invention provides a novel composition comprising a hybrid of decellularized cardiac tissue matrix capable of sustaining cellular growth combined with a plurality of mammalian cardiac cells (i.e., cells derived from cardiac tissues), including, but not limited to, myocytes, fibroblasts, endothelial cells, smooth muscle cells, etc., which can be used for a wide variety of research, diagnostic, screening, and therapeutic purposes.

In accordance with further embodiments, the present invention provides a novel composition comprising a hybrid of decellularized cardiac tissue matrix, capable of sustaining cellular growth and providing cues for cell alignment, combined with cardiac cells, which can be used for a wide variety of research, diagnostic, screening, and therapeutic purposes.

In accordance with another embodiment, the present invention provides a composition comprising a 3D biocompatible decellularized mammalian cardiac tissue matrix capable of sustaining cellular growth and a plurality of mammalian cardiac cells.

In accordance with another embodiment, the present invention provides a method for screening a substance for its effect on cardiac cells comprising: a) obtaining the composition disclosed herein; b) administering to the composition of a) with the substance; and c) determining the effect of the substance on the composition of a) by comparing the effect of the substance on the composition of a) to the effect of a control substance on the composition of a).

In accordance with another embodiment, the present invention provides a method for screening a substance for its effect on cardiac cells comprising: a) obtaining the composition disclosed herein; b) administering to the composition of a) with the substance; and c) determining the effect of the substance on the composition of a) by comparing the effect of the substance on the composition of a) to the effect of a control substance on the composition of a).

The EHS of the present invention allows long-term culture of cardiac cells, maintains contractile function, and prevents delamination of cells from the surface, a problem with conventional tissue culture on flat surfaces. Thus far, the inventors have cultured engineered heart slices of the present invention for more than 200 days. Long-term maintenance of cardiac cells from pluripotent sources may be necessary to ensure electrophysiological and structural maturation of the cells.

Thus, the EHS of the present invention are capable of surviving in culture for at least 75 days, or 100 days or 200 days or more.

In accordance with a further embodiment, the present invention provides a method for investigating the propensity of arrhythmia and abnormal contraction in cardiac myocytes (CM) derived from human induced pluripotent stem cells (hiPSCs) having a cardiac disease selected from the group including arrhythmogenic right ventricular dysplasia/cardiomyopathy (ARVD/C), long QT syndrome (LQTS), catecholaminergic polymorphic ventricular tachycardia (CPVT) and dilated and hypertrophic cardiomyopathy, comprising: a) obtaining a composition comprising a 3D biocompatible decellularized mammalian cardiac tissue matrix capable of sustaining cellular growth and a plurality of hiPSC-CM derived from patients having the cardiac disease; b) testing the composition of a) for the propensity of arrhythmia and abnormal contraction; and c) determining the propensity of arrhythmia of the composition of a) by comparing the propensity of arrhythmia on the composition of a) to the propensity of arrhythmia of a control composition having hiPSC-CM derived from healthy patients.

In accordance with still another embodiment, the present invention provides a composition comprising a 3D biocompatible decellularized mammalian cardiac tissue matrix capable of sustaining cellular growth, differentiation, proliferation and maturation, a plurality of mammalian cardiac myocytes and a plurality of fibroblasts or myofibroblasts.

In accordance with a further embodiment, the present invention provides a method for investigating the mechanism of fibrosis induced arrhythmia on cardiac myocytes (CM) comprising: a) obtaining a composition comprising a 3D biocompatible decellularized mammalian cardiac tissue matrix capable of sustaining cellular growth, a plurality of CM, and a plurality of fibroblasts or myofibroblasts; b) testing the composition of a) for the propensity of arrhythmia; and c) determining the propensity of arrhythmia of the composition of a) by comparing the propensity of arrhythmia on the composition of a) to the propensity of arrhythmia of a control composition lacking myofibroblasts.

The stacking provides several advantages. First, it enhances the integrity and contractile strength of the construct if used as a tissue patch. Second, the interdigitated spaces provided by the ECM layer will allow the flow of fluid and perfusion of the cellular layers (10B). Third, by including endothelial cells in some or all of the cell layers, they have the potential to form new blood vessels in the layer, or even migrate into the ECM layer (10C). In the case of an implanted construct, vasculature from the host tissue may also infiltrate the ECM layer and connects to the nascent blood vessels formed within (10D).

FIGS. 11A-11D show optical recording of transmembrane voltage in EHS created from NRVMs. EHS from rat and pig ECM were optically mapped after 5-7 days in culture. The slices were stained with voltage-sensitive dye (10 μM di-4-ANEPPS) and visualized with a 100×100 pixel Ultima-L CMOS camera (SciMedia), with motion inhibited by blebbistatin. Activation maps (11A) and signal traces (11B) show anisotropic propagation in EHS from rat ECM during 1 Hz field stimulation. Signal in 11B is from location marked by black dot in 11A. Activation map (11C) for EHS from pig ECM showed anisotropic propagation during 2 Hz point stimulation. Activation maps in 11A and 11C have 5 ms isochrones (located at the border between colors). White pulse symbol indicates site of the stimulus electrode. Black dot marks location of recording in 11D. White lines and values show the calculated longitudinal and transverse conduction velocity (CV) vectors.

Figure 12:
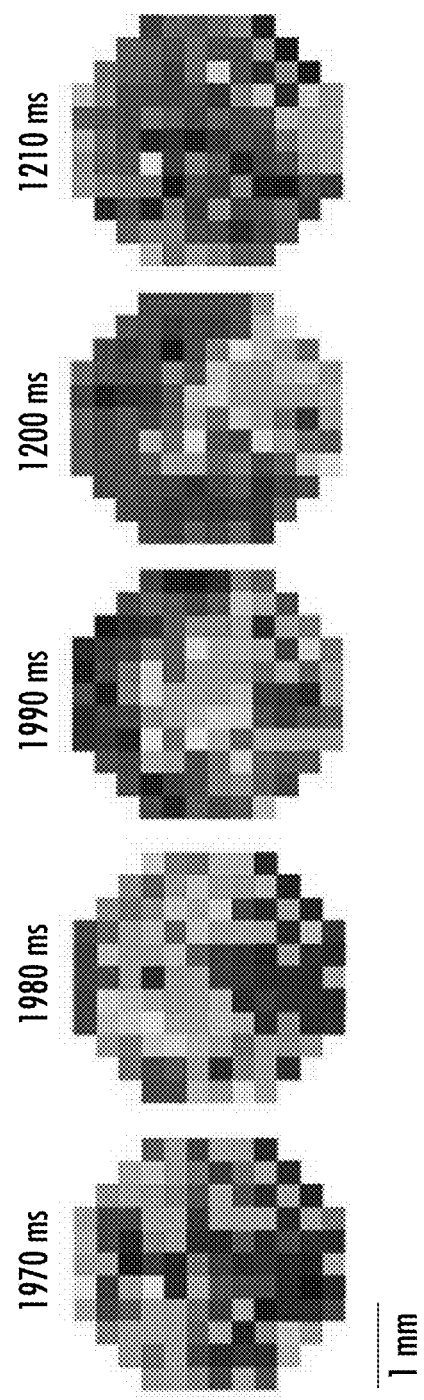

FIG. 12 shows optical recording of transmembrane potential in EHS created from human embryonic stem cell derived cardiomyocytes (hESC-CMs) differentiated after 28 days and then cultured for 4 days on decellularized rat slice stained with di-4-ANEPPS. Recordings were obtained during 1 Hz pacing and are shown 10 ms apart, with blue areas indicating resting membrane potentials and red areas indicating peak potentials.

Figure 13:
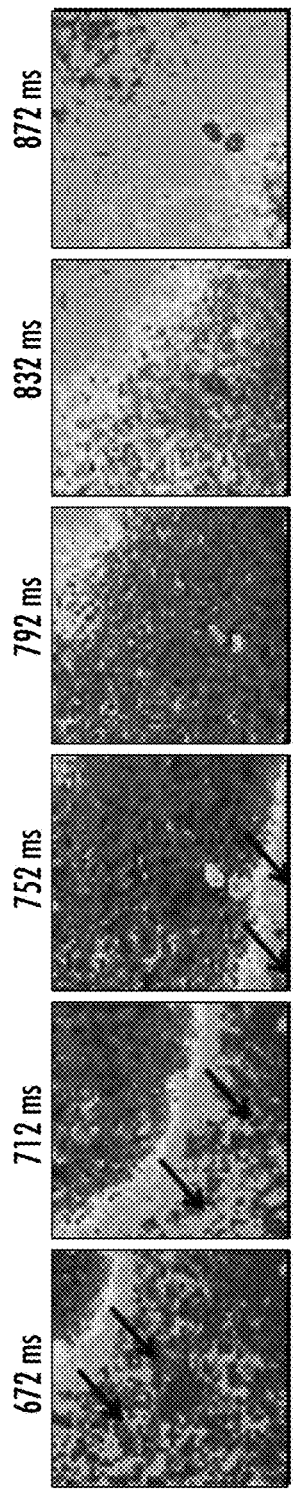
Figures 14A, 14B, 14C, 14D, 14E, 14F, 14G, 14H, 14I, 14J:
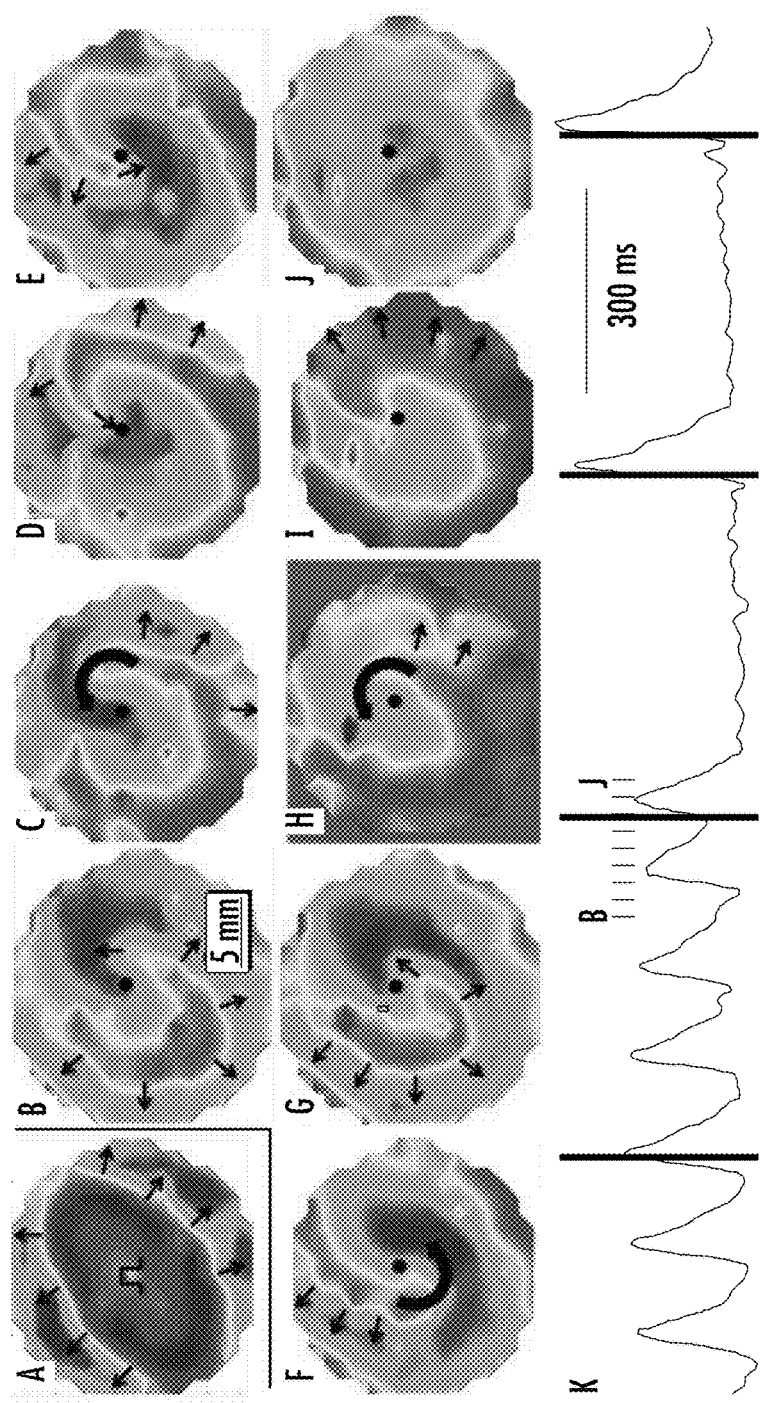
Figures 15A, 15B, 15C, 15D, 15E, 15F, 15G, 15H:
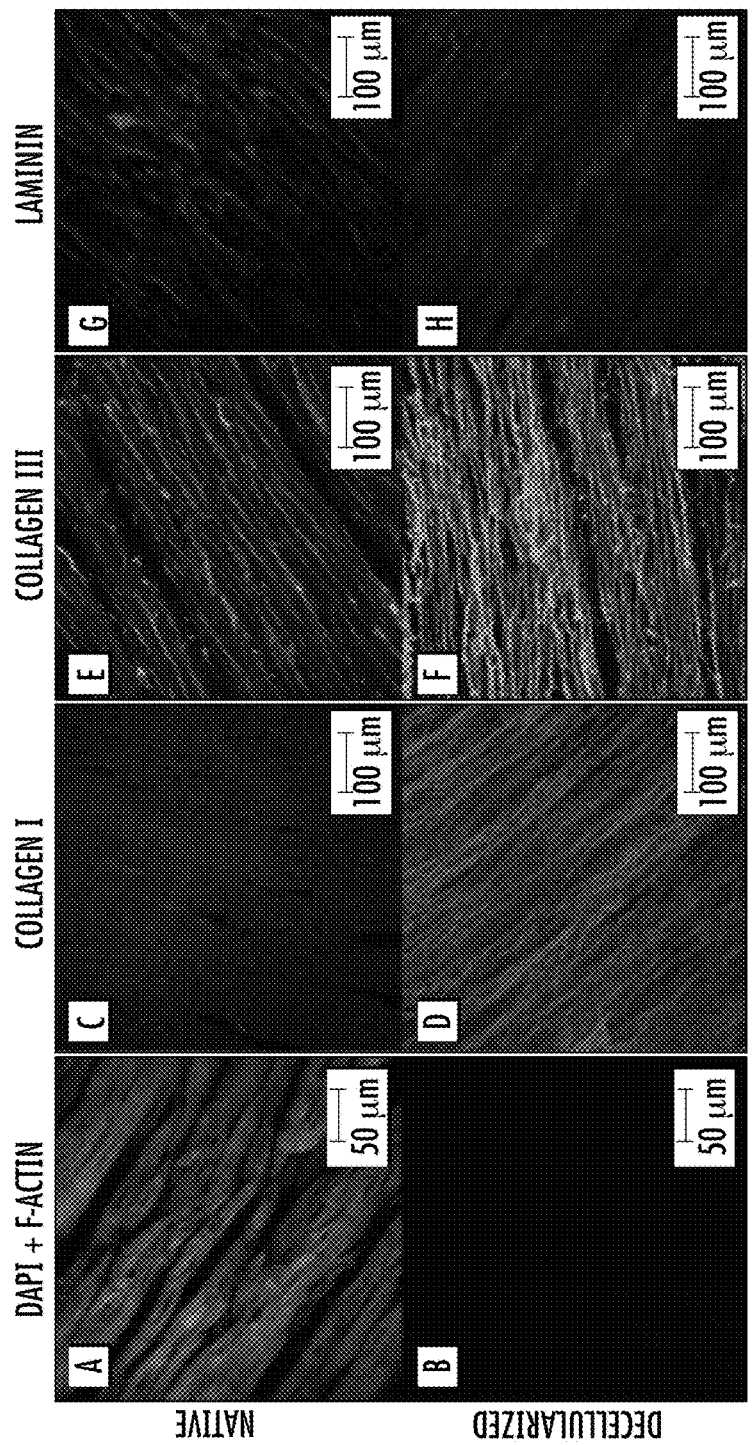

FIG. 13 shows optical voltage mapping of hESC-CM in EHS created from hESC-CMs. Snapshots at 6 different instants of time of 1.1 cm×1.1 cm area of H9-derived hESC-CMs. (hESC-CMs) were cultured for 52 days on 12 mm diameter, 300 μm-thick slices of decellularized porcine myocardium. Slices were stained with voltage-sensitive dye (10 μM di-4-ANEPPS) and visualized with a 100×100 pixel Ultima-L CMOS camera (SciMedia), with motion inhibited by blebbistatin. Recordings were taken 40 ms apart, with blue areas indicating resting membrane potentials and red areas indicating peak potentials, and arrows indicating direction of electrical propagation.

FIGS. 14A-14J show reentrant activity in EHS made from pig ECM. EHS produced homogeneous anisotropic conduction at 500 ms cycle length (CL) (14A). Pulse symbol indicates site of the stimulus electrode. A counterclockwise spiral wave was induced after pacing at 120 ms CL. Voltage maps taken 25 ms apart show reentry (14B-14G). Four 24 V/cm electrical shocks were applied, the second of which (14H) terminated the spiral wave (14I-14J). Small arrows show movement of AP wavefront. Thick curved arrows show propagation around the central core of the spiral wave. 14K shows the entire sequence of applied shocks (gray lines) and the optical voltage recording from the location marked by the small black dot in 14B-14J. Small black tick marks indicate when the snapshots in 14B-14J were taken.

FIGS. 15A-15H show the characterization of decellularized slices. Immunostaining of slices for F-actin (green) and DAPI (blue) indicates the presence of cellular content before (15A) but not after (15B) decellularization. The extracellular matrix components collagen I (15C and 15D), collagen III (15E and 15F), and laminin (15G and 15H) are present in the slice both before (top row) and after (bottom row) decellularization. All of the ECM components form aligned fibers.

Figures 16A, 16B, 16C:
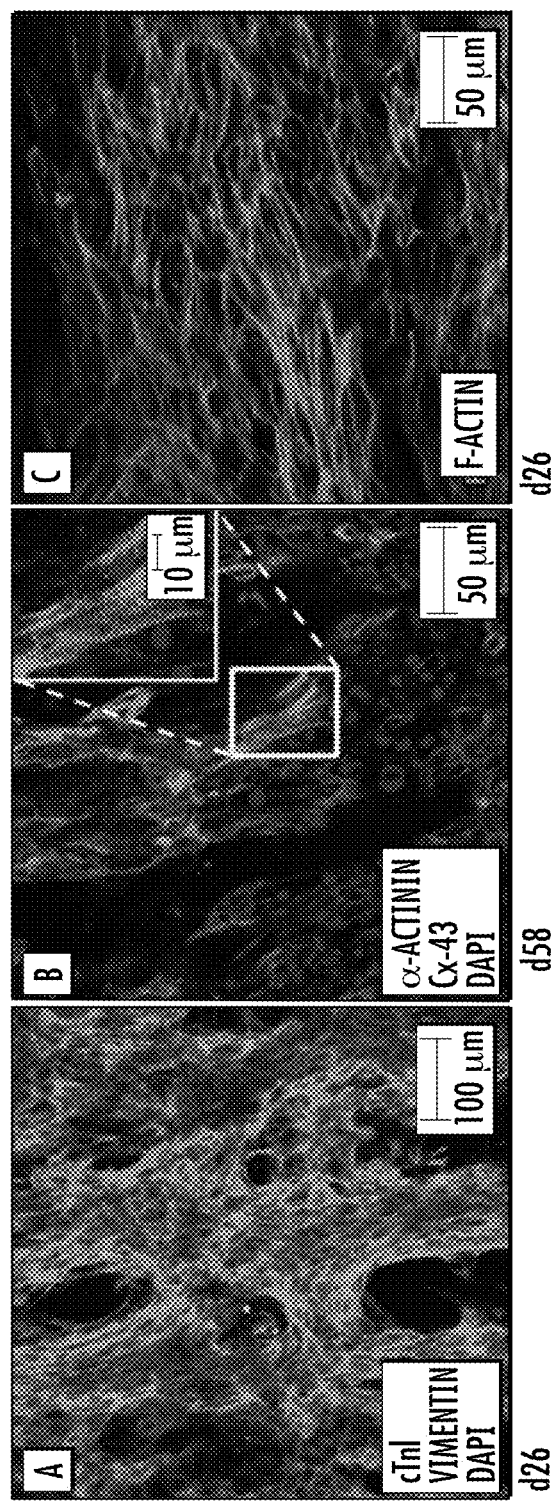

FIGS. 16A-16C show the morphology of hiPSC-CMs in EHS. Immunostaining for cardiac troponin I (green), DAPI (blue) and vimentin (magenta) reveal alignment of hiPSC-CMs (A). Aligned cardiomyocytes stained for α-Actinin (green) are connected by gap junctions, as indicated by Cx-43 (red) staining (B). A higher-magnification view demonstrates the presence of cardiomycoytes with striations typical of sarcomeric structures (B, inset). Staining for F-actin (C) further demonstrates cellular alignment and elongation. hiPSC-CMs were cultured in EHS for either 16 days or 48 days (day 26 or 58 of differentiation, respectively). White box in panel B corresponds to area magnified in inset.

Figures 17A, 17B:
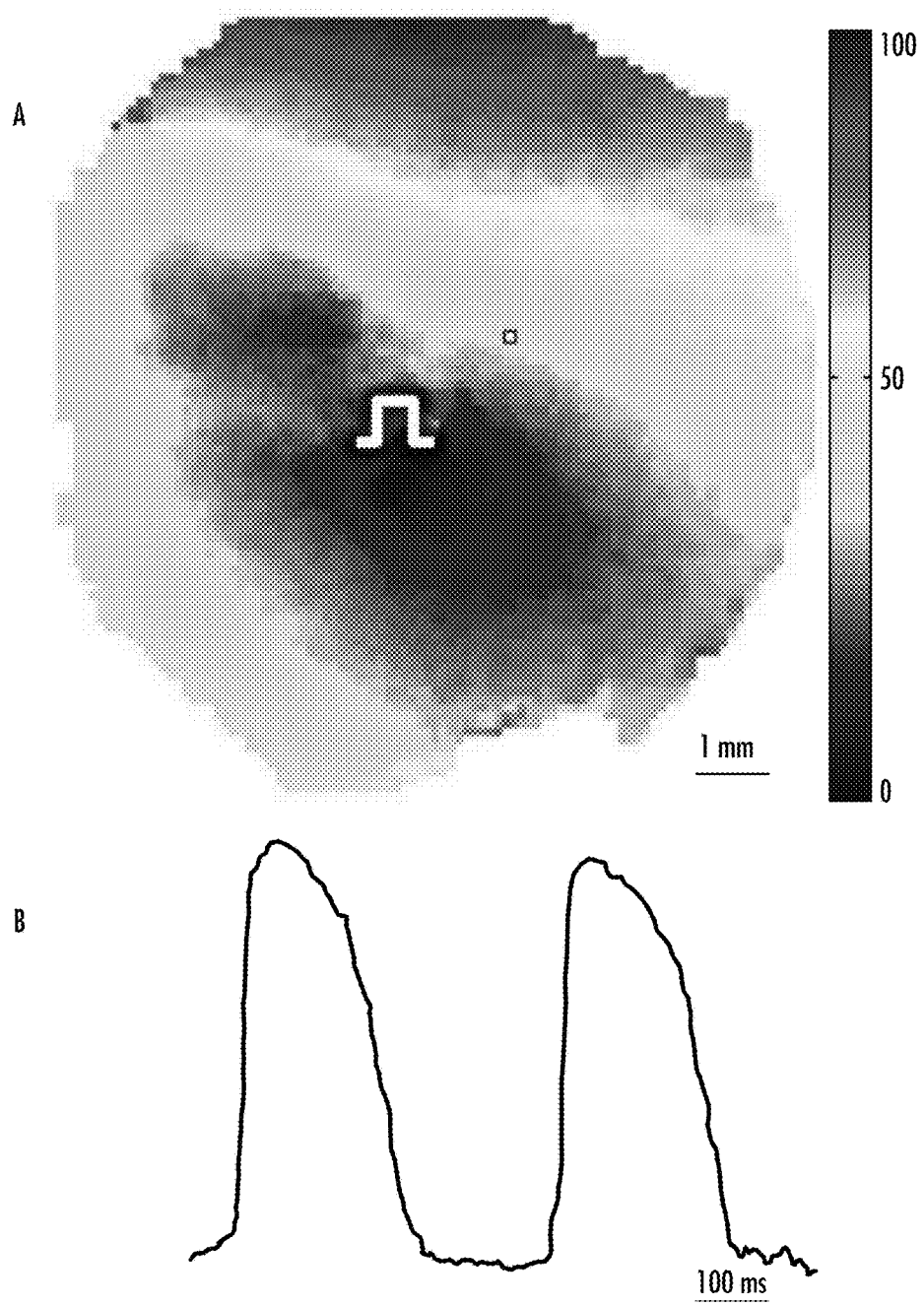
Figures 18A, 18B, 18C, 18D:
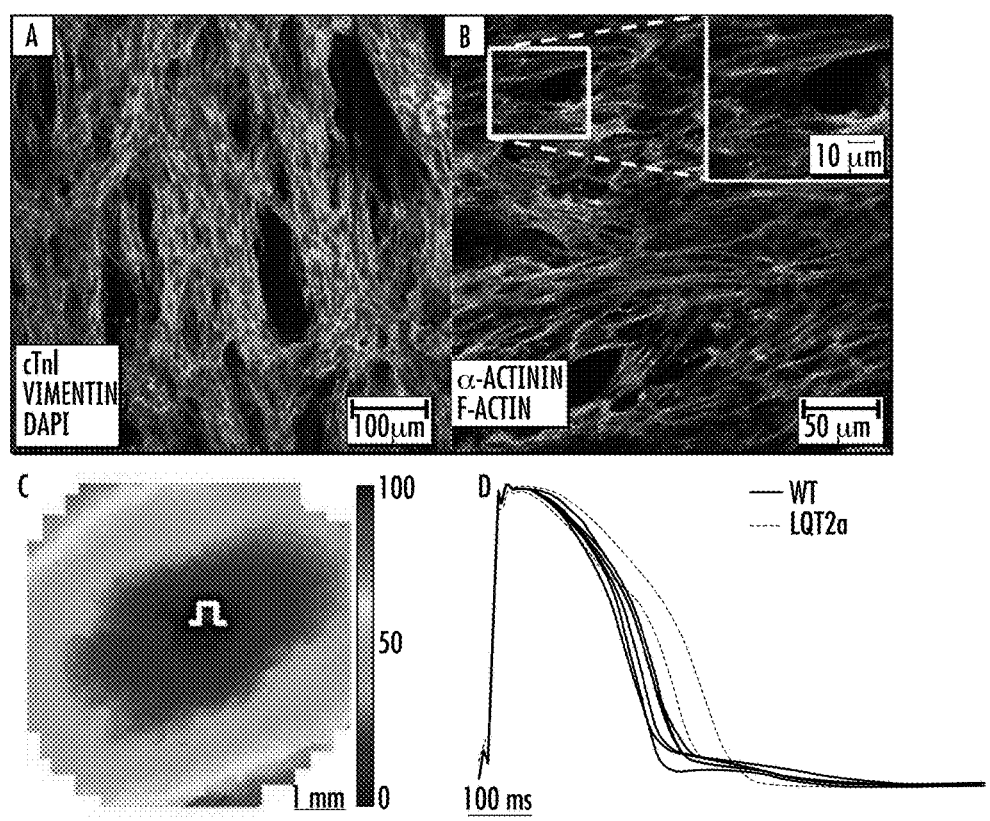
Figures 19A, 19B, 19C, 19D:
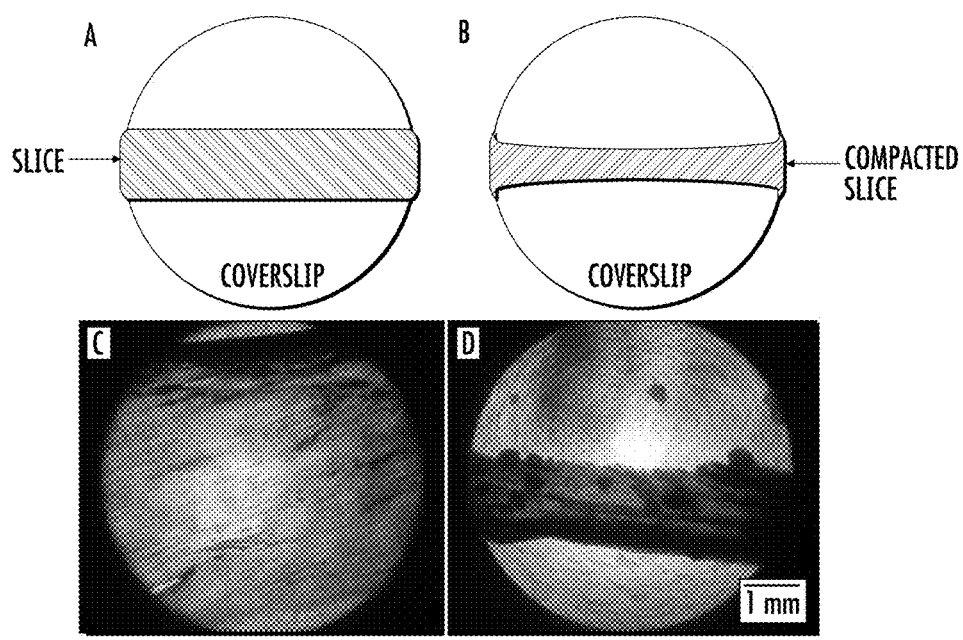

FIGS. 17A-17B show optical recording of transmembrane voltage in EHS created from wild-type hiPSC-CMs. A sample activation map (A) illustrates anisotropic propagation of electrical activity in an EHS paced at 500 ms cycle length. Sample voltage traces are shown for the site indicated by a white square (B).

FIGS. 18A-18D show. EHS made with LQTS hiPSC-CM. Immunostaining for cardiac troponin I (green), DAPI (blue) and vimentin (magenta) reveals alignment of hiPSC-CMs (A). Cardiomyocytes stained with α-Actinin (green) and F-actin (red) have striations typical of sarcomeric structures (B, inset). Activation map of EHS with LQT2a hiPSC-CMs paced at 1000 ms CL indicates anisotropic conduction (C). Average traces for wild type (blue) and LQT2a (black) EHS indicate differences in action potential morphology (D).

FIGS. 19A-19D depict compaction of EHS. Slices cut into rectangles or ovals will be decellularized, attached to a coverslip at each end, and seeded with cells (A). During culture, the cells will compact the matrix into a narrow strip (B). An oval slice attached to a coverslip is shown without any cells (C) for comparison to a similar slice that was seeded with differentiated induced pluripotent stem cells and cultured for 21 days to form a compacted strip (D). The compacted strip contracted spontaneously in culture and could be electrically stimulated.

DETAILED DESCRIPTION OF THE INVENTION

In accordance with an embodiment, the inventors have developed a novel composition of human engineered heart slices (EHS)—a hybrid of decellularized tissue and organotypic heart slice technology. Intact mammalian hearts are precision cut to obtain thin slices, which are decellularized and seeded with mammalian cells, including myocytes and cardiac myocytes which can be from a variety of sources.

In accordance with one or more embodiments, the present invention establishes a new standard for investigative studies of mammalian cells, including for example, myocytes, on or in a 3D decellularized matrix of EHS. In some embodiments, the combination of EHS and cells provides a means for studying disease including, patient-specific, genetic, neuronal, muscle, vascular, and cardiac related diseases at a functional, tissue level. The present invention provides a novel platform for the study of muscle and cardiac related diseases, including cardiac conduction dysfunction and arrhythmias for example.

Decellularized tissue matrix derived from native cardiac tissue retains the complex anisotropic structure of the myocardium and is a three-dimensional scaffold of extracellular matrix (ECM) proteins. The structure, surface topology, and composition of native ECM plays an important role in influencing a variety of cell processes, such as cell differentiation. Individual ECM components, including laminin, fibronectin, and various collagens have been found to regulate stem cell fate and somatic cell phenotypes, but more complex ECM systems favor cell maturation. Because native ECM exhibits a "dynamic reciprocity" with resident cells, decellularized matrix retains the signature of specific cell types and can also retain a variety of growth factors. Furthermore, ECM degradation products can provide important signaling molecules. Thus, ECM provides important topological, biochemical, molecular and mechanical cues which regulate CM function.

Figure 1:
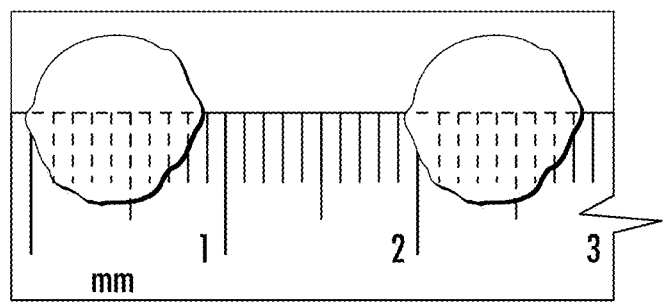
FIG. 1 illustrates a 300-μm thick slice of adult rat ventricle (top) or pig ventricle (bottom), before (left) and after (right) decellularization.
Figure 1:
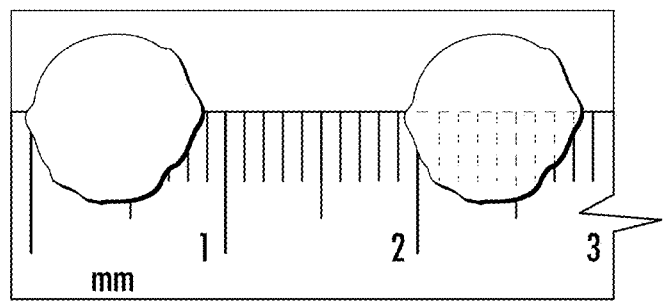

While entire animal hearts can be decellularized, repopulation of the whole tissue with cardiac cells remains a difficult challenge. The alternative to whole heart is the use of precision-cut, organotypic heart slices. Like the intact heart, heart slices possess a preserved tissue structure, recapitulating the in-vivo cardiac microenvironment. Current vibratome technology makes it possible to obtain slices of adult rat, mouse, guinea pig, rabbit and human heart tissue from fetal or surgical specimens with a precision of 1 μm (FIG. 1).

The method of decellularization of cardiac tissue slices is not limited to detergent treatment, but can include any method that removes cells from the extracellular matrix, including freeze-thawing, mechanical disruption, enzymatic treatment, or treatment with apoptosis-inducing agents.

The EHS of the present invention can be stored using a variety of means. After decellularization, slices can be lyophilized, flash frozen, or treated with fixatives for long-term storage. Slices can be reconstituted prior to reseeding with cells. The structure (alignment) of the extracellular matrix is retained throughout the storage process.

The EHS can be cut to a range of thicknesses of between about 10 μm to about 900 μm, preferably in the range of about 200 μm to about 300 μm. The slices have a diameter in a range of about 5 mm to about 30 mm, although these are not absolute limits. The size of the EHS used depends on the intended use. One of the novel advantages of the EHS of the present invention over the art is the thinness of the EHS slices. The thin slices allow for less time needed for decellularization which provides superior growth support for the cells on the matrix as the proteins and composition of the ECM are subjected to less chemical treatment and thus, less degradation.

In accordance with some embodiments, the methods of sectioning the EHS is not limited to using the vibratome, and can include the use of microtomes, cryostats, and dermatomes. In addition, in some embodiments, one of ordinary skill in the art would understand that the slicing of the EHS of the present invention can also be done at a variety of temperatures to change the stiffness of the tissue, which is necessary to control to prevent distortion of the tissue while cutting.

In accordance with some embodiments, the EHS of the present invention can be derived from various sources and age of tissues to manifest the normal or pathological function of the source tissues. For example, EHS can be obtained from cardiac tissue from different regions of the heart (the atria, right ventricle, septum, etc.) to capture elements of chamber specific disease, such as atrial fibrillation. They can be obtained from hearts of different ages to determine the effect of aging, or from diseased hearts to establish the effect of extracellular matrix composition on cardiac cell function and to create models of cardiac development or disease. Either animal hearts, or for relevance to human physiology and disease conditions, human hearts can be used.

The cells may be either allogeneic or xenogeneic in origin. The compositions can be used to deliver cells of species that are genetically modified.

It will be understood to those of ordinary skill in the art that the EHS matrix can be useful for 3D culturing of a wide variety of mammalian cell types apart from cardiac myocytes. The directionally oriented EHS matrix is suitable for culturing many cell types which have an orientation when in vivo in their natural tissue environments. Examples of such cell types include, but are not limited to, muscle cells, such as striated muscle and smooth muscle myocytes, neuronal cells, including motor neurons, stromal cells such as fibroblasts, and vascular endothelial cells. Culturing conditions for use with growth and maintenance of these cell types with the EHS of the present invention are known by those of skill in the art.

Figures 10A, 10B, 10C, 10D:
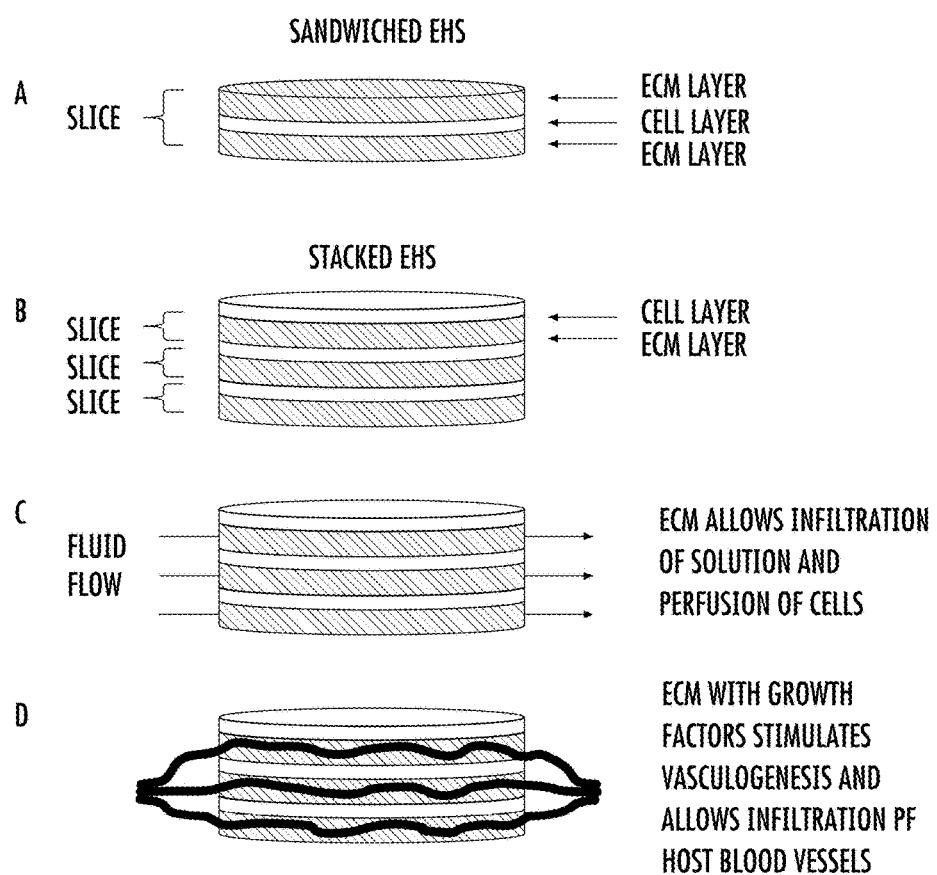
FIGS. 10A-10D depict a stacked embodiment of EHS. Multiple EHS can be stacked to create thicker constructs (10A). Each EHS consists of a cell layer (containing cardiac cells) and a decellularized extracellular matrix (ECM) layer.
Figures 11A, 11B, 11C, 11D:
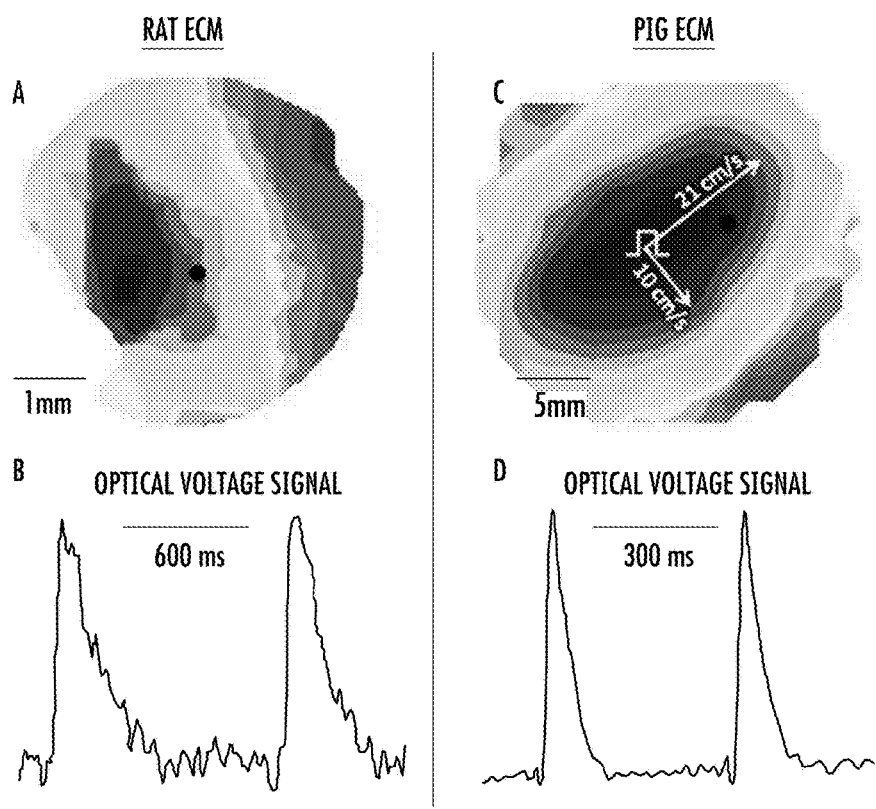

In accordance with an embodiment, the present invention provides a composition comprising at least two or more 3D biocompatible decellularized mammalian cardiac tissue slice matrices as described herein, wherein the first tissue slice matrix is populated with a plurality of cells on one surface of the first matrix, and the second tissue slice matrix is overlaid on the cells on the surface of the first matrix. An exemplary embodiment is shown in FIG. 10A. It will be understood that in some embodiments, there can be a plurality of layers of these matrices with layers of cells positioned in between the tissue slice matrices.

In accordance with another embodiment, the present invention provides a composition comprising a "stacked" cell and matrix composition. The composition provides at least two or more 3D biocompatible decellularized mammalian cardiac tissue slice matrices as described herein, wherein the at least two or more tissue slice matrices are populated with a plurality of cells, and wherein the first tissue slice matrix having the plurality of cells on the upper or top surface of the matrix, is positioned on top of a second issue slice matrix having the plurality of cells on the upper or top surface of the second tissue slice matrix. In other embodiments, there can be three, four, five, or more layers of tissue slice matrices populated with cells. In some embodiments, the cells in the different layers can be the same or different. In some embodiments, the tissue matrices can have different growth factors or other active agents in the different layers. Some exemplary embodiments are depicted in FIGS. 10B-10D.

In some embodiments, the additional decellularized mammalian cardiac tissue slice matrix is capable allowing the flow of fluid and perfusion of the tissue slice matrices populated with a plurality of cells (FIG. 10C). In some other embodiments, the additional decellularized mammalian cardiac tissue slice matrix further comprises growth factors. In some further embodiments, the growth factors include endothelial cell growth factors capable of inducing vasculogenesis, either from endothelial cells in the cell layer or from host tissue in the case of implantation of the instrument (FIG. 10D).

In some other embodiments, the reseeding or cell population of the EHS can be modified. For example, as described below, in an embodiment, better uniformity of reseeding, through the thickness of the slice, can be achieved by various means that improve cell penetration. Such means can include the addition of biologically active agents to the matrix to promote chemotaxis of the cells into the slice, and also includes physical means, such as centrifugation, mechanical stretch of the slice, magnetic forces, hydraulic pressure and flow, or agitation in a spinner or roller flask.

In addition, cells and or/chemical agents can be repeatedly added to engineered heart slices over time in order to increase the thickness of the preparation to form a more functional cardiac patch.

In some embodiments, the EHS can be coated with extracellular matrix proteins to supplement the native matrix of the decellularized slice and improve attachment of cells. Cells can also be suspended in hydrogels containing extracellular matrix proteins and added on top of the slice to produce more uniform seeding and improvements in cell survival and function.

Figures 2A, 2B, 2C:
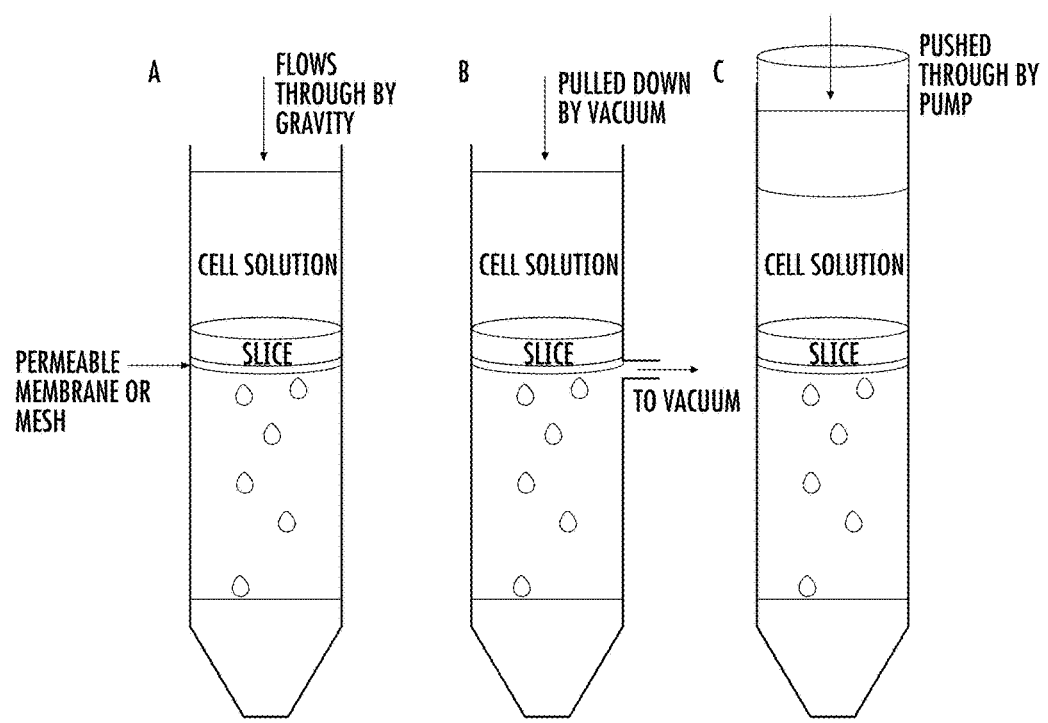
FIGS. 2A-2C show populating the EHS with cells by flowing cells through the EHS. The decellularized slice are placed on top of a permeable membrane or mesh and a suspension of cells is forced through it by allowing gravity (which can be enhanced by centrifugation) to move the solution down through the slice (2A), applying vacuum to draw the solution through the slice (2B), or using a pump to move the solution through the slice (2C). The method can also be used to decellularize the slice by substituting digestion medium (detergents, enzymes, physical means, other) for the cell solution.

The cells can be reseeded or populated onto the EHS in a variety of ways known to those of ordinary skill in the art. For example, as shown in FIGS. 2A-2C, the cells can be reseeded by flowing cells through the slice. The decellularized slice is placed on top of a permeable membrane or mesh, and a suspension of cells will be forced through it by allowing gravity (which can be enhanced by centrifugation) to move the solution down through the slice (A), applying vacuum to draw the solution through the slice (B), or using a pump to move the solution through the slice (C). These methods can also be used to decellularize the slice by substituting decellularization medium (detergents, enzymes, physical means, other) for the cell solution.

Figures 3A, 3B, 3C:
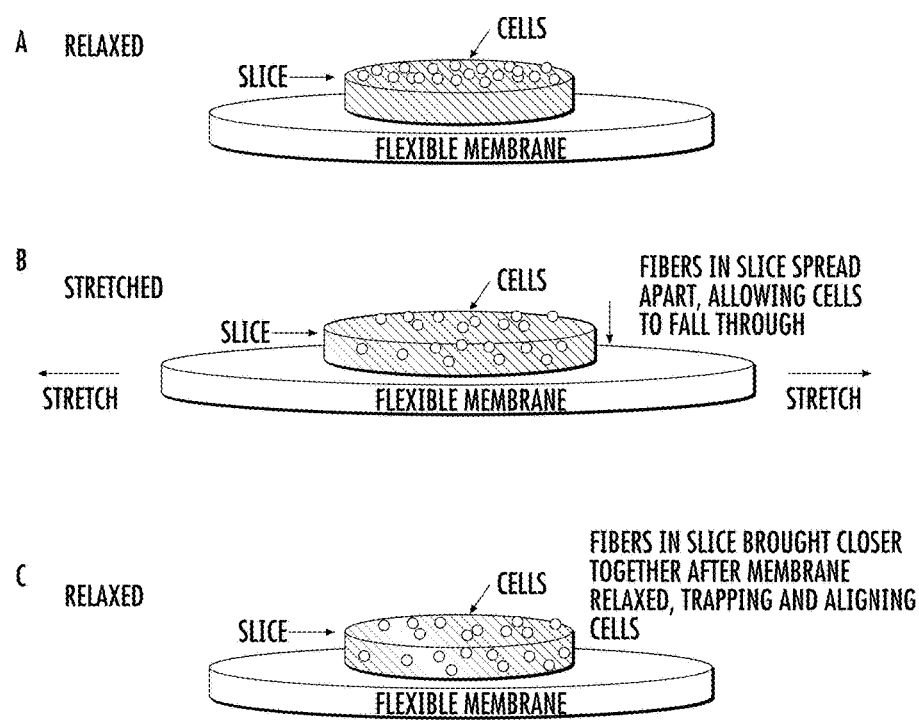
FIGS. 3A-3C depicts populating the EHS with cells during stretching. The decellularized slice is attached to a flexible membrane, and cells will be added on top of it (3A). The membrane is stretched (either uniaxial or biaxial stretch can be applied), spreading apart fibers in the slice and opening up spaces for the cells to move into (3B). Relaxation of the membrane traps the cells within the slice matrix when the fibers are brought back to their original configuration (3C). Compression of the aligned fibers can also help to align the cells. Stretching and relaxing of the membrane can be repeated cyclically to draw more cells into the slice.

In accordance with another embodiment, the EHS of the present invention can be reseeded while the EHS is stretched (FIGS. 3A-3C). The stretched fibers of the EHS allow cells to move into the interior of the slice and then when tension is relaxed, the cells are entrapped and aligned with the fibers in the slice. The stretching can be performed in one or two directions (uniaxial, or biaxial), and can be done with EHS stacked on top of each other in layers. Stretching and relaxing of the membrane can be repeated cyclically to draw more cells into the slice.

Figures 4A, 4B, 4C, 4D:
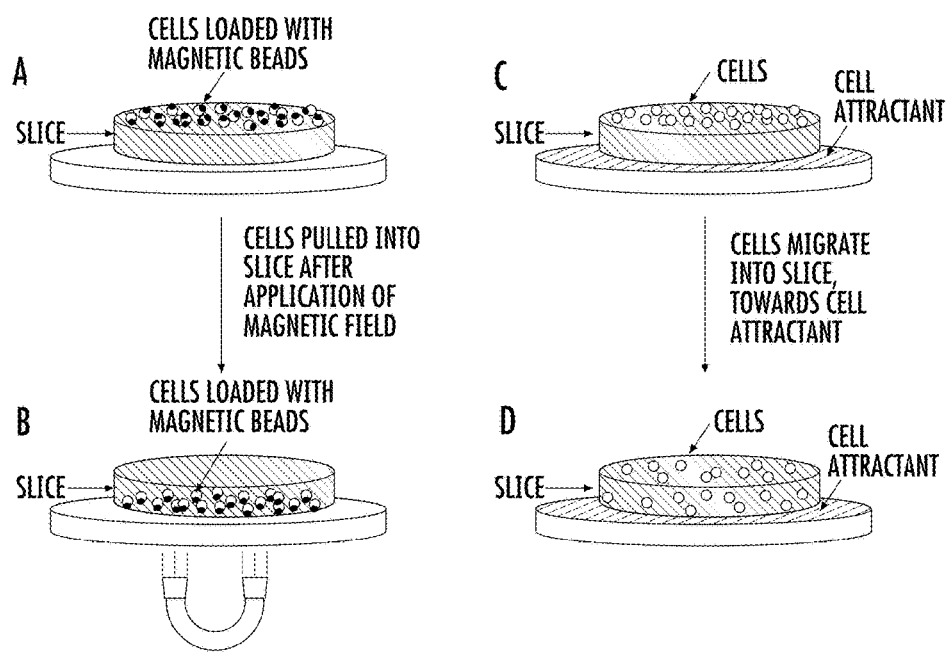
FIGS. 4A-4D depict populating the EHS with cells using magnetic fields and chemoattractant means respectively. Cells are loaded with magnetic beads and placed on top of the decellularized slices (4A). Application of a magnetic field will draw the cells into the slice (4B). A cell attractant (e.g., a growth factor or chemoattractant, for example) is coated on a coverslip and the decellularized slice will be attached on top of it (4C). Cells will migrate into the slice matrix toward the attractant (4D).
Figures 5A, 5B, 5C, 5D:
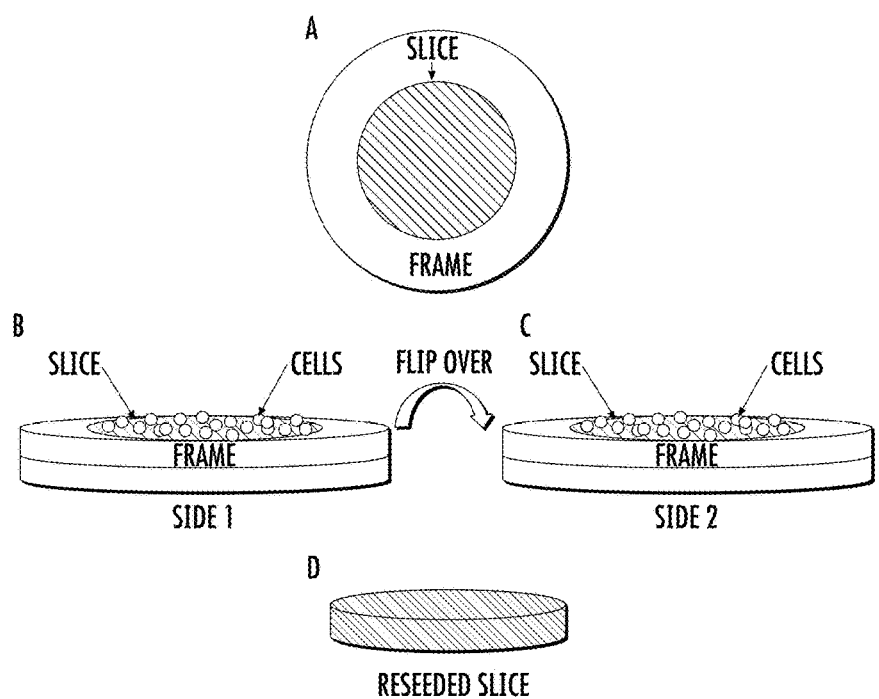
FIGS. 5A-5D show populating the EHS with cells on top and bottom surface of the EHS. The decellularized slice is attached within a substrate or frame (e.g., a glued plastic ring on either side of the slice, two magnetic rings on either side of the slice, PDMS or agarose solidified around the slice, etc.) that exposes both the top and bottom surfaces of the slice in the center (5A). Cells are seeded on the top of the first surface of the slice (5B). The frame, along with the slice, is then inverted, and cells are seeded on the second surface (5C), resulting in a slice recellularized with cells throughout the thickness (5D).

In accordance with an embodiment, the EHS of the present invention can be reseeded by applying magnetic field (FIGS. 4A-4B). Cells are loaded with magnetic beads and placed on top of the decellularized EHS slices (A). Application of a magnetic field will draw the cells into the slice (B).

In accordance with a further embodiment, the EHS of the present invention can be reseeded through the use of cell attractants (e.g., growth factors or other chemoattractant molecules) (FIGS. 4C-4D). One or more cell attractants will be coated on a coverslip, and the decellularized slice will be attached on top of it (A). Cells will migrate into the slice matrix toward the attractant (B).

In accordance with another embodiment, the EHS of the present invention can be reseeded on both the bottom and top "sides" of the slice. As shown in FIGS. 5A-5D (ppt4), the decellularized slice are attached within a frame means (e.g., a glued plastic ring on either side of the slice, two magnetic rings on either side of the slice, PDMS or agarose solidified around the slice, etc.) that exposes both sides of the slice in the center (A). Cells are seeded on the first or top of one side of the slice (B). The frame, along with the slice, is inverted and cells are seeded on the second or bottom side (C), resulting in a slice recellularized with cells throughout the thickness (D) of the slice.

Figures 6A, 6B:
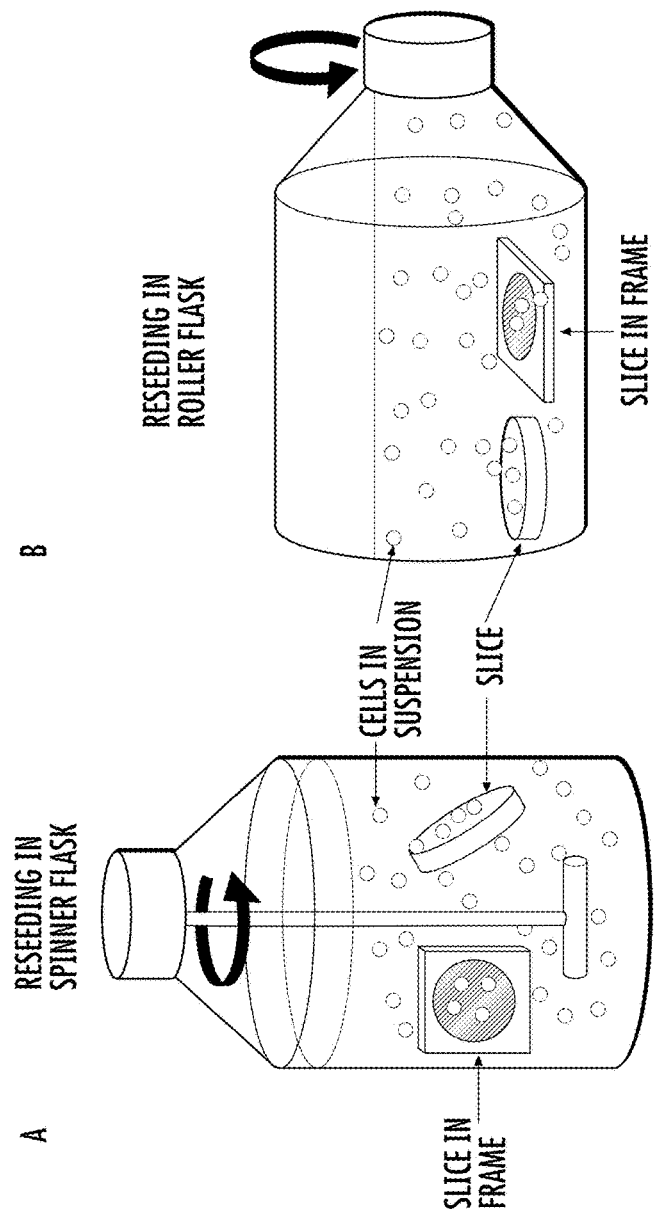
FIGS. 6A-6B depict populating the EHS by agitation of the EHS in cell suspension. Slices, either free-floating, attached to a coverslip, or within a frame are placed in a suspension of cells in a spinner flask (6A) or a roller flask (6B). The cell suspension and slices will be swirled around, allowing cells to attach to both sides of the slice for more uniform seeding throughout the matrix.

In accordance with a further embodiment, the EHS of the present invention can be populated with cells by agitation of one or more slices in a cell suspension. For example, EHS, either free-floating, attached to a coverslip, or within a frame are placed in a suspension of cells in a spinner flask (FIG. 6A) or a roller flask (FIG. 6B). The cell suspension and slices will be swirled around, allowing cells to attach to both sides of the slice for more uniform seeding throughout the matrix. It will be understood by those of skill in the art that variations of these processes including different containers, cell media, etc. can be used in the inventive methods.

In some other embodiments, CMs can be derived from differentiated hiPSCs from patients harboring any of a variety of genetic diseases such as arrhythmogenic right ventricular dysplasia/cardiomyopathy (ARVD/C), long QT syndrome (LQTS), catecholaminergic polymorphic ventricular tachycardia (CPVT), dilated cardiomyopathy (DCM), hypertrophic cardiomyopathy (HCM), or other general or acquired diseases including atrial fibrillation (AF), various forms of congestive heart failure (CHF), ventricular tachycardia (VT), cardiac hypertrophy, and cardiac fibrosis.

Figures 7A, 7B, 7C:
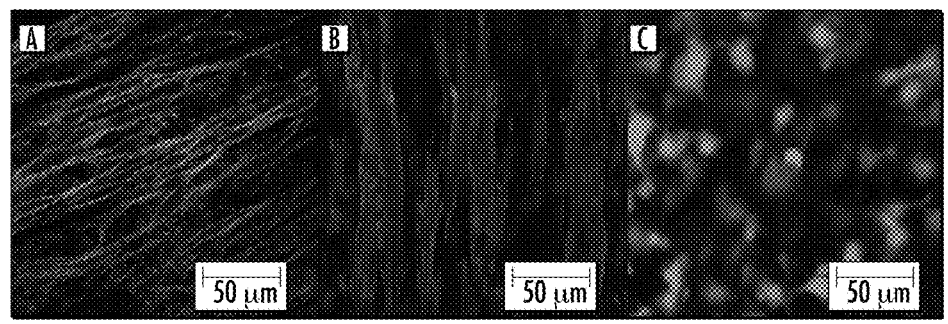
FIGS. 7A-7C show NRVMs cultured for 7 days on 300 μm thick slices of decellularized rat (7A, 7B) or pig (7C) myocardium. Staining is for 7A) DAPI (blue) and F-actin (green), 7B) DAPI (blue), cTnT (green), and vimentin (magenta), and 7C) live (green) and dead (red) cells. Z-stack images (not shown) show multiple layers of cells.
Figure 8:
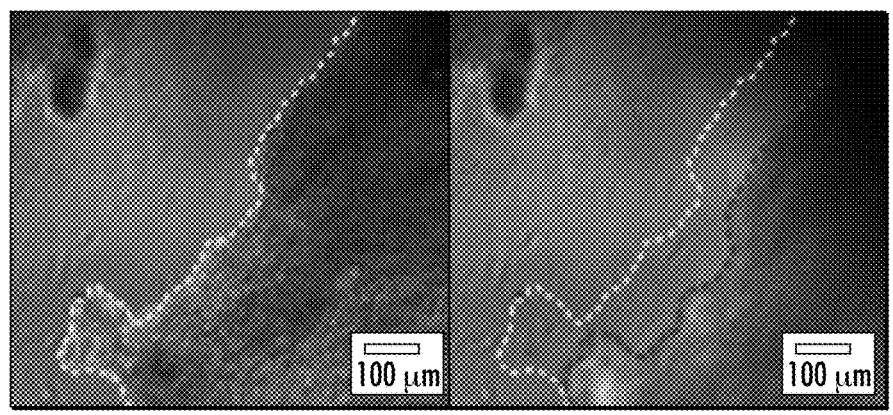
FIG. 8 depicts contraction of EHS. Neonatal rat ventricular myocytes (NRVMs) were cultured for 5 days on decellularized pig slice (300-μm thick, 5-mm diameter). Edge of EHS is outlined during rest (left image, dashed white line) and at peak contraction (right image, dashed red line), showing robust shortening of the construct. Construct was spontaneously contracting, but was responsive to electrical pacing.

Cardiomyocytes seeded on decellularized cardiac slices penetrate into the matrix, display an elongated morphology (FIG. 7), develop concerted contractions after several days in culture (FIG. 8), and even near the surface experience 3D matrix cues. hiPSC-CMs grown in this natural 3D environment can remodel the surrounding matrix and to acclimate to the foreign environment.

In some embodiments, stem cells or cardiac progenitor cells can be seeded on the EHS matrix of the present invention and migrate into it, resulting in a deep layer of densely distributed cells. Similarly, fibroblasts or other motile stromal cells can also be seeded. These stromal cells can then be directly transdifferentiated into cardiomyocytes or reprogrammed into hiPSCs and then differentiated into cardiomyocytes, resulting in a thick cardiac construct.

In addition, stiffness of the EHS substrate is highly influential on cellular properties, and in the slice cells experience physiological levels of stress, strain and anisotropy, which have been shown in numerous studies to be optimal for their growth and development. Recapitulation of physiological levels is difficult to achieve in synthetic polymer scaffolds, which must also match other design constraints such as biocompatibility, porosity and degradation rate; these naturally occur in decellularized slice matrices.

In some aspects, the EHS of the present invention can be immobilized in several ways: attaching the edges to a substrate (a coverslip, for example), framing the slice (by applying a magnetic ring or using a biocompatible polymer frame, for example), wrapping the slice around a three-dimensional scaffold, or embedding the slice in a material, either before it is sectioned as part of the tissue plug or after it is sectioned. It is understood that any of these methods could be applied before or after decellularization in order to maintain the original extracellular matrix conformation and prevent the slice from deforming, allowing for uniform cell seeding and ease of study.

Figures 9A, 9B:
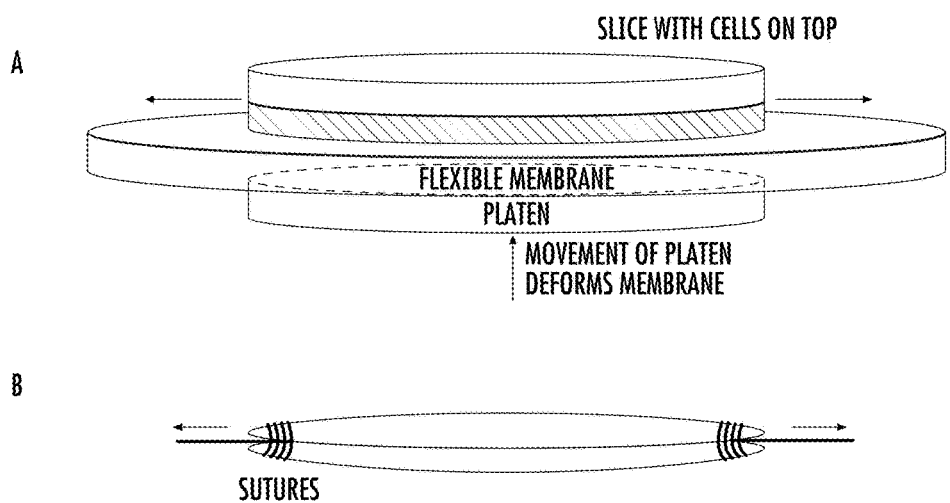
FIGS. 9A-9B show the mechanical conditioning of EHS. Uniaxial or biaxial strain can be applied by attaching EHS to a flexible membrane. This membrane is pulled over a platen that deforms the membrane and stretches it (9A). Strain can be applied by pulling directly on the EHS. The EHS is tied at each end using sutures that can be immobilized for static strain, pulled on to apply strain, or attached to force transducers (9B).

In accordance with some embodiments, the EHS of the present invention can be mechanically conditioned (FIG. 9). For example, the EHS can be attached to an elastic substrate (e.g. —thin silicone membrane) by any of a number of means, including biocompatible adhesives, electrostatic, or chemical covalent bonding. Following attachment of the slice, uniaxial or biaxial mechanical strain can be applied to the slice by stretching the elastic substrate, for example, over a rigid platen (9A). The rate or magnitude of the applied strain can be controlled by increasing/decreasing how fast or how far the membrane is pulled over the platen, respectively. The uniformity and anisotropy of the applied strain can be controlled by modifying the shape of the platen (i.e. —circular platen for applying equibiaxial strain along the radial and circumferential directions). Alternatively, the slice can be stretched directly (9B).

In accordance with some other embodiments, the EHS of the present invention can be subjected to controlled compaction. For example, wherein the EHS is affixed at specified points on the substrate, and has a plurality of unaffixed edges that can be compacted by cells after reseeding. Compaction can be used to improve alignment of cells within the preparation and improve electrical conduction and force generation in the slice (FIG. 19).

In accordance with some embodiments, the EHS in combination with one or more cell types can be cultured in "stacks" (FIGS. 10A-10C). Stacking can take the form of a decellularized slice on top of an EHS that has been reseeded, effectively sandwiching the cells between layers of extracellular matrix. This allows the cells to be surrounded by extracellular matrix and experience a three-dimensional environment. As an example of an embodiment, the EHS of the present invention can be defined as having an upper or "top" surface, and a lower or "bottom" surface which is located on the opposite side of the slice from the "top" surface. For example, one or more EHS having a layer of myocytes on its top surface, can layered on the top surface of a second EHS also having a layer of cells on its top surface. In some embodiments, the cells of the second or further slices can have the same or different cell type layered on each EHS. In an embodiment, a stack of EHS can comprise one or more EHS layers having cardiac myocytes, wherein the layers of EHS with cardiac myocytes alternate with EHS layers having a different cell or combination of cell types, such as, for example, vascular endothelial with or without smooth muscle cells, thereby defining a vascularized myocyte implant. Alternating layers of EHS with fibroblasts with layers of EHS seeded with cardiac myocytes can be a means of changing (increasing) the stiffness. It will be understood by those of ordinary skill in the art, that stacks of EHS such as described herein can be used for a variety of tissue engineering uses, including grafts, tissue repair and replacement. There can be stacks having two, three, four or more layers, which is only limited by the use envisioned for the implant.

In some alternative embodiments, the EHS can be detached from the substratum, allowed to roll up and grown as tube-like structures. These tubes can be constructed with cells aligned along the long axis of the tube, in effect producing a hollow muscle. Such tubes will generate contractile force along the long axis. The tubes can also be constructed with cells aligned along the circumferential direction, which could result in a squeezing or pumping effect on the luminal contents.

In some embodiments, the EHS compositions of the present invention can be conditioned. For example, decellularized slices from animal hearts can be reseeded with human fibroblasts, which will remodel the composition of the extracellular matrix. These slices will be decellularized once more, leaving behind a slice that has human matrix components and retains the organization of the initial slice. This is a strategy to make human-compatible matrix by starting with slices of animal hearts, which are a more readily available tissue source.

In some embodiments, the EHS compositions of the present invention can also include one or more biologically active agents. An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

Further examples of biologically active agents include, without limitation, enzymes, receptor antagonists or agonists, hormones, growth factors, autogenous bone marrow, antibiotics, antimicrobial agents, and antibodies. The term "biologically active agent" is also intended to encompass various cell types and genes that can be incorporated into the compositions of the invention.

When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

Buffers, acids and bases may be incorporated in the compositions to adjust pH. Agents to increase the diffusion distance of agents released from the composition may also be included. Buffering agents help to maintain the pH in the range which approximates physiological conditions. Buffers are preferably present at a concentration ranging from about 2 mM to about 50 mM.

In some embodiments, compositions disclosed herein may be positioned in a surgically created defect that is to be reconstructed, and is to be left in that position after the reconstruction has been completed. The present invention may be suitable for use with local tissue reconstructions. In one embodiment, the repair of damaged tissue may be carried out within the context of any standard surgical process allowing access to and repair of the tissue, including open surgery and laparoscopic techniques. Once the damaged tissue is accessed, a composition of the invention is placed in contact with the damaged tissue along with any other surgically acceptable patch or implant, if needed.

In accordance with one or more embodiments, the EHS compositions of the present invention can be used to treat a variety of tissue defects and diseases, including, for example diseases of the heart. Examples of some cardiac diseases which can be ameliorated using implants of EHS compositions of the present invention include re-entrant arrhythmias associated with ARVD/C, LQTS, CPVT, AF, VT and cardiac fibrosis or mechanically failing tissue associated with DCM, HCM, ARVD/C or other forms of CHF. The EHS compositions can be grown in vitro and then surgically implanted in resected portions of the diseased organ.

In some embodiments, the EHS matrix can be derived from human donor tissue. For example, tissue can be resected from the heart of the patient, and EHS can be made from the tissue using the methods disclosed herein. The EHS can then be used as a matrix with cardiac myocytes derived from human embryonic stem cells or hiPSC from healthy family members or from the patient him or herself, the latter becoming an autologous cardiac implant.

Timed electrical stimulation and mechanical stretch can be used to improve the maturation and functionality of the EHS. They also provide clinically relevant signaling cues that may be important in the evolution and manifestation of cardiac diseases, such as ARVD/C, LQTS, CPVT, DCM, HCM, AF, CHF, VT, cardiac hypertrophy and cardiac fibrosis.

In accordance with a further embodiment, it is contemplated that making EHS matrix from fibrotic cardiac tissue and reseeding with healthy cells can complement the already mentioned fibrosis model by allowing comparison of cells on fibrotic extracellular matrix and healthy extracellular matrix.

The EHS compositions of the present invention comprising myocytes or other electrically active cells can be studied using a wide variety of electrophysiological techniques including patch clamp, microelectrode arrays, and voltage and calcium dyes in concert with optical imaging. The EHS compositions comprising myocytes can also be studied using methods that measure contraction of the cells on the matrix using a variety of techniques including compaction of gels, miniature force transducers, and traction force microscopy.

Characterization of human CMs derived from hiPSCs consists of expression assays of CM-specific genes and proteins. However, functional studies have evolved for basic electrophysiology and contraction and more recently, for monogenic models of cardiac channelopathies and cardiomyopathy. The use of optical mapping in the methods of the present invention will elevate the electrophysiological characterization, as well as the functional status of these cells, in general, from that of a single cell to the multicellular behavior of large populations of electrically coupled cells. Optical mapping data of neonatal rat EHS (FIG. 11) or of human embryonic stem cell derived cardiomyocytes (FIGS. 12, 13) as described herein show that EHS is a tissue-like construct that can be electrically stimulated to fire action potentials that propagate as electrical wavefronts.

Unlike approaches using the intact heart, the EHS of the present invention avoids constraints of cell delivery and minimizes the difficulty arising from cell washout, so that accurate assessments of cell survival and cell-cell coupling can be made. The amount of cell survival (live/dead cell stain and cell counts) can be quantified as well as size/shape of the cells (image analysis). Gap junctions between cells can be examined by immunolabeling with antibodies against connexins, and adherens junctions by antibodies against cadherins.

Because a hallmark of some cardiac diseases such as ARVD/C, HCM and CPVT is their susceptibility to arrhythmias with exercise, in accordance with an embodiment, the EHS of the present invention can be subjected to adrenergic stimulation, mechanical stretch and increases in beat rate as relevant stress conditions.

In some embodiments, the compositions and methods of the present invention can be used to study pharmacological interventions of a variety of cardiac diseases. Use of other cardiotropic drugs and small molecules can also be tested using the methods and compositions of the present invention.

In an embodiment, the compositions and methods disclosed herein are used to test mechanisms of fibrosis-induced arrhythmias in ARVD/C myocytes. Late stages of ARVD/C are characterized by fibro-fatty infiltration that causes structural abnormalities. EHS can be engineered to mimic both aspects of this condition. As such, the ARVD/C EHS compositions of the present invention provide a greater understanding of the electrophysiological consequences of progression of this disease.

In accordance with some embodiments, the present invention can be provided as a kit comprising the EHS. In an example, a kit can contain a number of dried, frozen, and sterilized slices, which are prepared for storage and then capable of subsequent use with appropriate reconstitution. The end user can thaw the slices, rehydrate them with tissue culture medium, and then seed the slices with any desired cell type such as cardiac cells, skeletal muscle cells or smooth muscle cells.

The kits disclosed herein will include a container means for the EHS compositions of interest. The kit may include a delivery device. Instructions for their use can be included.

Uses for such kits include, for example, therapeutic applications. The invention provides kits for use in diagnosing or treating a disease or condition. For example, the kit may comprise an EHS composition as well as cardiac myocytes derived from any of a variety of stem cells, such as adult stem cells, mesenchymal stem cells, or hiPSCs.

EXAMPLES

Decellularization of tissue slices. The inventive methods use a procedure developed in our laboratory to obtain decellularized tissue slices from adult rat ventricles. Hearts are harvested from adult Sprague-Dawley rats, rinsed with deionized water using a Langendorff perfusion setup, and stored at −80° C. for a minimum of 16 hours. In an alternate embodiment, samples of pig ventricle are trimmed with dermal punches, the plugs are stored at −80° C. for a minimum of 16 hours, thawed and embedded in agarose, and sectioned using the vibratome. After thawing, atria and the base of the ventricles are removed, and the remaining ventricles are embedded in low gelling temperature agarose. The embedded heart is sliced at in a range of intervals, e.g. 300 µm intervals, parallel to the epicardium using a 7000smz vibrating microtome (Campden Instruments). Slices are trimmed to circular samples (e.g. 8 mm dia) using a dermal punch and decellularized using a protocol modified from Ott et al. (*Nat. Med.,* 2008; 14:213-21). Slices are treated with 1% SDS detergent (1.5 hours), deionized water (15 minutes), and 1% Triton X-100 (7 minutes) under constant agitation. In whole hearts, this results in <4% DNA retention, no significant change in GAG content, and no residual retention of SDS after 124 hour wash with PBS. The decellularized slices are rinsed overnight in PBS containing penicillin and streptomycin, flattened out and wrapped around plastic coverslips of varying sizes (e.g. 5 to 14 mm), and sterilized using ethanol prior to cell seeding. The size of the diameter of the slices can be varied in accordance with their use. For example, 12 mm slices can be made and applied to 12 mm diameter coverslips for study. Because the slices are very thin, washout of SDS occurs in less than 12 hours (FIG. 1).

Characterization of decellularized tissue slices. The quality of tissue decellularization is assessed by fluorescent imaging of nuclei stained with 4',6-diamidino-2-phenylindole (DAPI) and cytoskeletal actin stained with Alexa Fluor 488 phalloidin. Immunohistochemistry is used to evaluate and compare the distribution of collagen I and III, fibronectin, and laminin in the scaffolds to native tissue to assure that the composition of ECM is similar (FIG. 15), and electron microscopy will show the fiber structure of the ECM and any residual myofibers. The glycosaminoglycan (GAG) content is quantified using a spectrophotometric Safranin O assay. Residual DNA is assayed using the Quant-IT Assay Kit (Life Technologies).

Transcript and protein expression levels of the desmosomal genes encoding plakophilin-2 (PKP2), desmoplakin (DSP) and plakoglobin (JUP) are obtained; the latter is thought to be a relatively specific hallmark of ARVD/C (*Cardiovasc Pathol.* 2010; 19:166-70).

Ultrastructural images can be obtained of sarcomere organization, and immunofluorescent antibody labeling of structural and contractile proteins (α-actinin, troponin-I, β-MHC, MLC2a and MLC2v) can be performed.

Global (microarrays) and targeted (qPCR) gene expression analyses will provide insights into the mechanisms underlying ultrastructural changes and contractile isoform abundance.

Bioinformatic data analyses can examine mechanisms that may be involved in eliciting the observed phenotypes. Quantitative reverse transcription-polymerase chain reaction (qRT-PCR) can be used to assay the mRNA levels of the aforementioned structural and connective proteins, desmosomal proteins, as well as ion channel proteins (CACNA1C, HERG, SCN5A, HCN4 and KCNJ2) corresponding to the membrane ionic currents ($I_{CaL}$, $I_{Kr}$, $I_{Na}$, $I_f$ and $I_{K1}$, respectively) which are underdeveloped in cardiomyocytes cultured on flat substrates such as tissue culture plastic or ECM-coated glass coverslips.

Electrophysiology of EHS and isolated hiPSC-CMs. After a period of between about 1-4 weeks in culture, the EHS are stained with the voltage-sensitive dye, di-4-ANEPPS, and stimulated by electric field. Imaging is performed using a SciMedia Ultima-L CMOS camera (100×100 pixels) in an upright configuration, operating at 10 kHz frame rate. At 1× magnification (used in FIG. 11), the field of view is 11 mm×11 mm, resulting in a spatial resolution of 110 μm per pixel. Optical magnification of the system can be increased up to 7.9×, giving a spatial resolution of 14 μm and a field of view of 1.39 mm. High spatial resolution mapping with voltage-sensitive dyes allows the degree of synchrony between adjacent cardiomyocytes to be monitored, so that the seeding density can be optimized. The optical recordings of action potentials at individual cell-containing pixels are spatially and temporally filtered, baseline-corrected, and range-normalized. To prevent motion artifacts, the EHS can be bathed in the myosin-II inhibitor, blebbistatin. Examples of this approach using NRVM, hESC-CM or hiPSC-CM on the EHS of the present invention are shown in FIGS. 11-14, 17, and 18.

Electrophysiological function can be characterized by: beating rate, APD50 (action potential duration to time of 50% repolarization), APD90, range-normalized rate-of-rise, and range-normalized diastolic slope. Tissue-level function: spontaneous beat rate, cell excitability (strength-duration relation), cell refractoriness (strength-interval relation using programmed S1-S2 stimulation) and rate-dependent changes in action potential duration (APD restitution) also can be measured.

Electrophysiological and contractile functions of the myocytes grown on EHS can also be evaluated in isolated cells. EHS can be enzymatically dissociated, and individual cells can be patch clamped in whole-cell mode for the measurement of action potentials and whole cell currents, $I_{Na}$, $I_{CaL}$, $I_{Kr}$, $I_f$ and $I_{K1}$. These currents, as well as their mRNA transcript levels, can be compared with those from control cells (hiPSC-CMs from unaffected gene-negative family members and ESC-CMs). Cell shortening is used to quantify contraction.

One experimental limitation is the developmental heterogeneity of the hiPSC-CMs produced in culture. Although beating CMs are observed in monolayer cultures at day 7 of differentiation, the cultures are not uniformly but heterogeneously contractile until day 10. In an alternative embodiment, employing a lentivirus construct to select for ventricular cells (VCMs), eliminates contaminating atrial or nodal cells from the culture to promote more uniform patterns of contraction with well-defined ventricular cells. hESC-CMs and hiPSC-CMs demonstrate immature functionality, which can improve during long-term culture and passaging. Electrical pacing or mechanical stretch can be used to enhance or accelerate the maturation of these cells.

Propensity for arrhythmia in EHS. After about 4 weeks in culture, strength-duration and strength-interval relations are measured in both EHS and CMs isolated from EHS. Spatiotemporal maps of action potential propagation are obtained by staining the EHS with voltage-sensitive dye followed by optical mapping of propagated action potentials at a standard pacing rate of 1 Hz to determine CV. Additionally, the incidence rate for pacing stimuli to initiate reentrant arrhythmias in EHS is quantified by increasing the basal pacing rate in discrete steps from 0.5 to 3 Hz. The propensity for ectopic arrhythmia include mean number of spontaneous ectopic beats following a train of rapid stimulation, and for reentrant arrhythmia, includes magnitude and heterogeneity of conduction across the EHS, incidence rate of reentrant spiral waves, pacing rate for initiation, and persistence (duration) of reentry. These measures of arrhythmia can be compared to those of EHS derived from patients harboring clinically defined cardiac disease, and from EHS derived from unaffected family members and from isogenic cell lines as control groups.

For the case of ARVD/C, paralleling the electrophysiological experiments are protein assays of plakophilin-2, plakoglobin, and Cx43, obtained from EHS used in the optical mapping experiments, using both immunofluorescence staining and Western blots to determine the localization and total expression level, respectively, of these proteins.

Modulation by mechanical stretch. Some cardiac diseases such as ARVD/C, HCM and CPVT have enhanced likelihood of arrhythmia with exercise. Control EHS can be subjected to chronic cyclic mechanical stretch (up to 15% strain). This is achieved by attaching decellularized slices onto flexible-bottomed culture plates (BioFlex), which we have verified adhere to untreated StageFlexer membrane. The slices are seeded as before, and deformed using vacuum pressure with the FX-5000 Tension System (Flexcell International) for 48 hours after cell seeding. Live/dead assays are performed on EHS with and without 1 week of cyclic stretch prior to the 4-week time point. Also, the contribution of intrinsic mechanical contraction can be separated out by adding the contraction inhibitor, blebbistatin, during culture. Optical mapping and pacing protocols can be applied to determine slowing of CV and the incidence of reentrant arrhythmias. EHS can be dissociated enzymatically to obtain isolated hiPSC-CMs, and histological and molecular characterization, along with cellular electrophysiology, proceed as in the above procedures to determine whether cellular hallmarks of the disease are enhanced by mechanical stretch compared with unstretched EHS.

Because VT has been associated with late activating myocardium, this can be tested with EHS by electrically pacing the EHS at a fixed rate (1 Hz) and applying mechanical stretch just prior to the electrical stimulus (mimicking prestretch by early activating myocardium), compared with controls in which the EHS is unstretched. With the Flexercell system, sinusoidal or pulsatile waveforms can be used for stretch, and given partially out of phase with (in advance of) the stimulus pulse. Comparison groups are where stretch is in phase with the stimulus pulse, or is constant.

Modulation by sympathetic tone. Certain cardiac diseases such as ARVD/C, HCM and CPVT have enhanced likelihood of arrhythmia with exercise. Increase in sympathetic tone can be mimicked by chronic application of isoproterenol to EHS during culture. Conversely, load-reducing therapy is simulated by the application of the β-blocker propanalol. Conduction velocity (CV) as well as the incidence rate of VT is monitored via optical mapping as described above. Disease EHS are dissociated enzymatically to obtain isolated hiPSC-CMs, and histological and molecular characterization, along with cellular electrophysiology, proceeds as above to determine whether cellular hallmarks of the disease are modulated by β-adrenergic stimulation or blockade. As an alternate approach, chronic application of ACE inhibitors (ramipril, lisinopril, carvedilol, spironolactone, losartan) during culture can be tested, with the aim of determining whether structural and electrophysiological abnormalities are suppressed.

Recapitulation of a fibrosis-like state. Two essential components of fibrosis can be engineered into EHS compositions: (1) Myofibroblasts. Human ventricular fibroblasts (Lonza) are irradiated to prevent further proliferation, mixed in a ratio of 1:3 with hESC-CMs or hiPSC-CMs (similar to what the inventors did previously in their NRVM studies (*Circulation*. 2011; 123:2083-93)), and then plated onto decellularized tissue slices as in the above examples. Transforming growth factor-β (TGF-β), is a potent inducer of cardiac myofibroblast (CMF) differentiation both in vivo and in vitro, and is added during culture to fully induce the myofibroblast phenotype. EHS at the 4-week time point are stained with three-way combinations of fluorescent antibodies against prolyl-4-hydroxylase, α-actinin, α-smooth muscle actin (SMA), vimentin and DAPI and imaged using confocal microscopy. As control, TGF-β is added to EHS that have not been supplemented with fibroblasts. (2) Collagen. Extracellular collagen is secreted by myofibroblasts, but may not be sufficient to significantly alter matrix stiffness and mimic severe fibrosis. Towards that goal, collagen I (1 mg/ml) is added to the cell mixture prior to plating on the decellularized slices. After EHS formation, and following electrophysiological studies, collagen content is assayed to verify elevated levels. Alternatively, decellularized slices from hearts that are already fibrotic can be used.

Increased propensity of fibrotic EHS for ectopic and reentrant arrhythmia. After the standard 4 weeks in culture, fibrotic EHS are stained with voltage-sensitive dye (di-4-ANEPPS) and optically mapped. The propensity for ectopic and reentrant arrhythmia can be evaluated by rapidly pacing the EHS with or without additional chemical or mechanical stressors. For comparison, similar experiments will be conducted on non-fibrotic EHS as described in previous examples.

Contribution of electromechanical coupling from myofibroblasts. In fibrotic EHS, the direct proarrhythmic effect of myofibroblasts via electrical interactions with cardiomyocytes is tested by knockdown of connexin expression in the myofibroblasts by shRNA prior to their addition to the cardiomyocytes, and seeding onto the decellularized slices of the present invention to form fibrotic EHS. The direct proarrhythmic effect of myofibroblasts via mechanical interactions is tested by the separate addition of blebbistatin (myosin-II contraction inhibitor), low-dose gadolinium (stretch-activated channel blocker), or streptomycin (stretch-activated channel blocker) to the fibrotic EHS, which in the inventors' previous NRVM study relieved the electrophysiological suppression of conduction and reduced the severity of arrhythmia. In both scenarios, the slowing of conduction and incidence of ectopic and reentrant arrhythmia are compared with those for non-fibrotic EHS. Contraction of the myofibroblasts and its suppression by blebbistatin can be confirmed by traction force measurements.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An engineered heart slice (EHS) composition comprising a 3D biocompatible decellularized mammalian cardiac tissue slice matrix having an upper and a lower surface, wherein the EHS is mechanically conditioned by applying to it uniaxial or biaxial strain and wherein the matrix is being capable of sustaining cellular growth.

2. The composition of claim 1, wherein the cardiac slice matrix can be derived from one or more different regions of the heart.

3. The composition of claim 1, wherein the heart regions are selected from the group consisting of the atria, ventricles, septum, epicardium, midmyocardium, and endocardium.

4. The composition of claim 1, wherein the cardiac slice matrix is derived from one tissue or from multiple tissues of differing ages.

5. The composition of claim 1, wherein the cardiac myocytes are differentiated from a variety of cell sources, including mesenchymal stem cells, embryonic stem cells, induced pluripotent stem cells, cardiac progenitor cells, adipose-derived stem cells, peripheral blood-derived stem cells, cord blood-derived stem cells, adult stem cells, and reprogrammed fibroblasts.

6. The composition of claim 1, wherein the origin of the cardiac tissue slice matrix to be decellularized is selected from the group consisting of mouse, rabbit, rat, pig, dog, goat, sheep, cow, horse or human tissue.

7. The composition of claim 1, wherein the origin of the mammalian cells is selected from the group Consisting of mouse, rabbit, rat, pig, dog, goat, sheep, cow, horse and human tissue.

8. The composition of claim 1, wherein the composition includes two or more different cell types.

9. The composition of claim 1, wherein the composition further comprises one or more biologically active agents.

10. The composition of claim 1, further comprising a plurality of non-myocytes, including fibroblasts, myofibroblasts, endothelial cells or smooth muscle cells.

11. The composition of claim 1, wherein the origin of the myocytes is human.

12. The composition of claim 1, wherein the cells are capable of surviving in culture for at least 75 days, or 100 days or 200 days or more.

13. The composition of claim 1, wherein the tissue slice matrix is stored using a method selected from the group consisting of: lyophilization, flash freezing, and treating with fixatives.

14. The composition of claim 1, wherein the tissue slice matrix is immobilized on a substrate.

15. The composition of claim 1, wherein the tissue slice matrix is immobilized on a substrate using adhesives, sutures, electrostatic, or chemical covalent bonding.

16. The composition of 14, wherein the substrate includes a ring, a frame, a coverslip, or a hydrogel.

17. The composition of claim 14, wherein the EHS is affixed at specified points on the substrate, and has a plurality of unaffixed edges that can be compacted by cells after reseeding.

18. A composition comprising at least two or more 3D biocompatible decellularized mammalian cardiac tissue slice matrices of claim 1, wherein the first tissue slice matrix is populated with a plurality of cells on one surface of the first matrix, and the second tissue slice matrix is overlaid on the cells on the surface of the first matrix.

19. The composition of claim 18, wherein the composition further comprises at least one or more additional mammalian cardiac tissue slice matrices populated with a plurality of cells.

20. The composition of claim 19, wherein the cells in the two or more cardiac tissue slice matrices can be populated with different types of cells.

21. A composition comprising at least two or more 3D biocompatible decellularized mammalian cardiac tissue slice matrices of claim 1, wherein the at least two or more tissue slice matrices are populated with a plurality of cells, and wherein the first tissue slice matrix having the plurality of cells on the upper or top surface of the matrix, is positioned on top of a second issue slice matrix having the plurality of cells on the upper or top surface of the second tissue slice matrix.

22. The composition of 24, wherein the composition further comprises at least one or more additional mammalian cardiac tissue slice matrices populated with a plurality of cells.

23. The composition of 25, wherein the additional decellularized mammalian cardiac tissue slice matrix further comprises growth factors.

24. The composition of 26, wherein the growth factors include endothelial cell growth factors capable of inducing vasculogenesis.

25. The composition of claim 20, wherein the plurality of mammalian cells is selected from the group consisting of smooth muscle myocytes, striated muscle myocytes, cardiac myocytes, fibroblasts, neurons, vascular endothelial cells, cardiac progenitor cells and stem cells on at the at least one or more surfaces of the matrix.

26. The composition of claim 20, wherein the cardiac slice matrix can be derived from one or more different regions of the heart.

27. The composition of claim 20, wherein the heart regions are selected from the group consisting of the atria, ventricles, septum, epicardium, midmyocardium, and endocardium.

28. The composition of claim 20, wherein the cardiac slice matrix can be derived from one tissue or from multiple tissues of differing ages.

29. The composition of claim 20, wherein the cardiac slice matrix can be derived from one diseased tissue or from multiple tissues of differing cardiac disease states.

30. The composition of claim 20, wherein the cardiac myocytes are differentiated from a variety of cell sources, including mesenchymal stem cells, embryonic stem cells, induced pluripotent stem cells, cardiac progenitor cells, adipose-derived stem cells, peripheral blood-derived stem cells, cord blood-derived stem cells, adult stem cells, and reprogrammed fibroblasts.

31. The composition of claim 20, wherein the cardiac tissue is selected from the group consisting of mouse, rabbit, rat, pig, dog, goat, sheep, cow, horse or human tissue.

32. The composition of claim 20, wherein the origin of the mammalian cells is selected from the group consisting of mouse, rabbit, rat, pig, dog, goat, sheep, cow, horse or human tissue.

33. The composition of claim 20, wherein the origin of the mammalian cells is selected from the group consisting of mouse, rabbit, rat, pig, dog, goat, sheep, cow, horse or human tissue.

34. The composition of claim 20, wherein the composition includes two or more different cell types.

35. The composition of claim 20, wherein the composition further comprises one or more biologically active agents.

36. The composition of claim 20, further comprising a plurality of non-myocytes, including fibroblasts, myofibroblasts, endothelial cells or smooth muscle cells.

37. The composition of claim 20, wherein the origin of the myocytes is human.

38. The composition of claim 20, wherein the tissue slice matrix is immobilized on a substrate.

39. The composition of claim 1, wherein the composition further comprises a plurality of mammalian cells selected from the group consisting of smooth muscle myocytes, striated muscle myocytes, cardiac myocytes, fibroblasts, neurons, vascular endothelial cells, cardiac progenitor cells and stem cells on at least one surface of the matrix.

* * * * *